United States Patent [19]

Steudle et al.

[11] Patent Number: 4,891,968
[45] Date of Patent: Jan. 9, 1990

[54] PROCESS FOR THE DETERMINATION OF THE CONCENTRATION OF SUBSTANCES DISSOLVED IN A SOLVENT BY MEANS OF OSMOTIC CELLS

[75] Inventors: Ernst Steudle, Eckersdorf; Gerd Böling, Inden-Pier; Josef Zillikens, Jülich, all of Fed. Rep. of Germany

[73] Assignee: Kernforschungsanlage Julich Gesellschaft mit beschrankter Haftung, Julich, Fed. Rep. of Germany

[21] Appl. No.: 159,360

[22] Filed: Feb. 23, 1988

[30] Foreign Application Priority Data

Feb. 27, 1987 [DE] Fed. Rep. of Germany ....... 3706361

[51] Int. Cl.⁴ .............................................. G01N 13/04
[52] U.S. Cl. ...................................................... 73/64.3
[58] Field of Search ......................................... 73/64.3

[56] References Cited

U.S. PATENT DOCUMENTS 4,706,495 11/1987 Steudle et al. ...................... 73/64.3

FOREIGN PATENT DOCUMENTS 3525668 5/1986 Fed. Rep. of Germany ....... 73/64.3

Primary Examiner—John Chapman
Assistant Examiner—Joseph W. Roskos
Attorney, Agent, or Firm—Nils H. Ljungman

[57] ABSTRACT

This invention relates to a process and apparatus for the determination of the concentration of substances dissolved in a solvent. For this purpose, an osmotic cell is used, in which first, by means of an (external) reference solution, a working pressure is established, and after replacement of the reference solution by the solution to be tested, the pressure curve established in the cell is determined. The object is also to determine the concentrations of substance present in high concentration with very great absolute precision. For this purpose, an osmometer solution is selected which contains an excess of not more than 80 mOsm more than the reference solution, and in which the substances to be measured are contained in such a concentration that the difference of the concentrations of the substances in the solution to be tested and in the osmometer solution is not more than 70 mOsm. The total concentration of the substances is then determined taking into consideration the concentration of the substances in the osmometer solution. For the determination of very small deviations of the substances (less than 20 mOsm), the temperature of the solutions at the measurement point is kept constant, for which purpose there is provided an appropriate device.

22 Claims, 14 Drawing Sheets

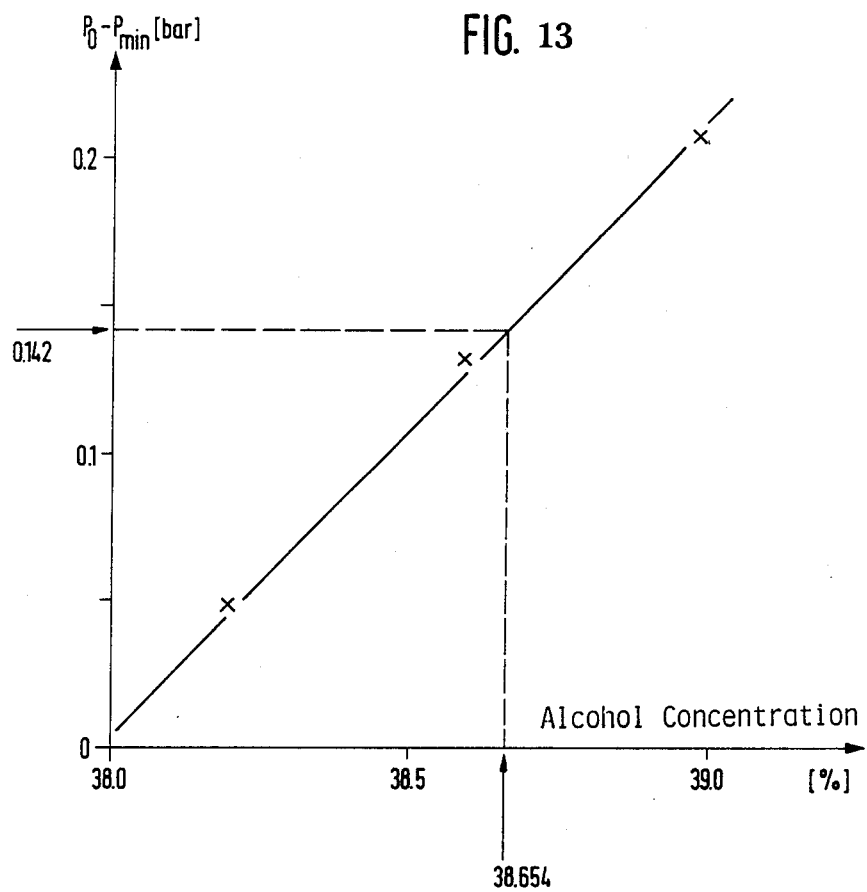

PROCESS FOR THE DETERMINATION OF THE CONCENTRATION OF SUBSTANCES DISSOLVED IN A SOLVENT BY MEANS OF OSMOTIC CELLS

BACKGROUND OF THE INVENTION

1. Field of the Invention:

This invention relates to a process for the determination of the concentration of substances dissolved in a solvent by means of an osmotic cell with a wall which is as rigid as possible, the osmotic cell being provided with pressure measurement devices for measurement of the hydrostatic pressure in the osmotic cell and the membrane of the osmotic cell having the highest possible conductivity for the solvent and exhibiting a sufficient retention capacity for the substances, by means of which the osmometer solution in the osmotic cell is brought into communication, through the membrane, with the solution to be tested for the concentration of substances, whereby first, using an appropriate solution placed in communication with the osmometer solution via the membrane as well as an appropriate osmometer solution, a working pressure $P_O$ is established and determined, whereupon, after replacement of the solution by the solution to be tested, the concentration of the impermeable substance or substances in the solution to be tested is determined from the pressure curve established in the osmotic cell.

This invention also relates to an apparatus for the determination of the concentration of substances dissolved in a solvent, the apparatus including at least one vessel and at least one measuring head, the measuring head comprising an osmotic cell with a pressure measurement device, which has a rigid metal or plastic wall and whose membrane exhibits the highest possible modulus of elasticity, the highest possible conductivity for the solvent, and a sufficient retention capacity for the substances in the solution to be tested, whereby the ratio of the volume of the osmotic cell to the effective surface of the membrane is a maximum of 0.2 mm, whereby the measurement head or heads can be immersed in the vessel, and whereby the vessel or containers can be filled with a solution (reference solution) to establish the working pressure $P_O$, with the solution to be tested and, if necessary, with standard solutions.

2. Description of the Prior Art:

The above-mentioned process and the apparatus are described in U.S. Pat. No. 4,706,495, which corresponds to German Laid Open Patent Appln. No. DE-OS 35 25 668. They are used for the determination of the concentration of substances in a solution, if two or more substances (one permeable in relation to the membrane and one or more impermeable substances) are in the solution. The above-mentioned documents are incorporated herein by reference as if the texts thereof were fully set forth herein.

U.S. Pat. No. 4,706,495, which corresponds to German Laid Open Patent Appln. No. DE-OS 35 25 668 describes the process (Process Ia), in which, after a sufficiently rapid exchange of the solution to be tested and the pure solvent, the pressure curve in the osmotic cell, the minimum pressure $P_{min}$ established and the subsequent final pressure $P_E$ are measured, whereupon the concentration of the impermeable substance or substances in the solution to be tested is determined on the basis of standard values from the pressure difference $P_O - P_E$ and the concentration of the permeable substance in the solution is determined from the difference $P_E - P_{min}$. The process can also be executed so that the concentration of impermeable ($C_{imp}^o$) substances and permeable ($C_s^o$) substance in the solution to be tested is determined by calibration of the measurement system with different solutions containing the impermeable and permeable substances in different, known concentrations, whereby for the determination of the permeable components, care must be taken that the standard solution contains the impermeable substance in approximately the same concentration as the solution to be tested, whereby the concentration of permeable substance is taken from the graph $(P_E - P_{min}) = f(C_s^o)$ and the concentration of impermeable substances is taken from the graph $(P_O - P_E) = g(C_{imp}^o)$. $(P_O - P_E) = g(C_{imp}^o)$ represents a straight line in each case, while $(P_E - P_{min}) = f(C_s^o)$ can deviate from the linear form, since $t_{min}$ is a function of the mixing ratio $\sigma_s \cdot C_s^o C_{imp}^o$.

U.S. Pat. No. 4,706,495, which corresponds to German Laid Open Patent Appln. No. DE-OS 35 25 668 also describes a process (Process Ib) in which, after the exchange of the solution to be tested and the solvent, the minimum pressure $P_{min}$ established in the osmotic cell, the time $t_{min}$, within which the minimum pressure $P_{min}$ is established, the rate constant $k_s$ for the exponential pressure increase which occurs following the minimum pressure and the final pressure $P_E$ established after the pressure increase are determined. Then, the concentration $C_s^o$ of the permeable substance s is determined from the equation $$P_E - P_{min} = \sigma_s \cdot RT \cdot C_s^o \cdot \exp(-k_s \cdot t_{min}) \tag{1}$$

where $R = 8.31434$ J/K° mol,

T = absolute temperature and $\sigma_s$ = reflection coefficient of s and the concentration ($C_{imp}^o$) of the impermeable substance or substances is determined from the equation $$P_O - P_E = RT \cdot C_{imp}^o \tag{2}$$

In the execution of the known processes, the most rigid possible osmotic cell is used, i.e., an osmotic cell with a rigid wall and a rigid membrane, so that during the execution of the process, the change in the volume of the osmotic cell is negligible. Under these conditions, equations 1 and 2 apply.

If, however, the membrane and the osmotic cell are not sufficiently rigid, and the change in the volume of the osmotic cell during the measurement is not negligible, the modulus of volume elasticity $\epsilon$ is determined by means of an appropriate device (for example, a control rod and a micrometer, and through use of an appropriate formula set forth herein), and the concentration $C_s^o$ of the permeable substance is determined from the equation $$P_E - P_{min} = \frac{\epsilon}{\epsilon + RT \cdot C_{imp}^i} \cdot \sigma_s \cdot RT \cdot C^o{}_s \cdot \exp(-k_s \cdot t_{min}) \tag{3}$$

while the concentration $C_{imp}^o$ of the impermeable substance is determined from the equation $$P_0 - P_E = \frac{\epsilon}{\epsilon + RT \cdot C_{imp}^i} RT \cdot C^o{}_{imp} \tag{4}$$

The membrane to be used for the Processes Ia and Ib should exhibit the greatest possible conductivity for the solvent and a sufficient retention capacity for the substances. [As used herein, "retention" capacity refers to the reduced permeability that the membrane of the osmotic cell to the substances to be measured, as opposed to its much greater permeability vis a vis the solvent. Alternatively, the "rejection" capacity of the membrane embraces the same concept.] The retention capacity of the membrane is sufficient for the substances if the exchange of the permeable substance through the membrane is delayed by the membrane in relation to the exchange of the pure solvent through the membrane, so that during the exchange phase of the pure solvent, the exchange of the permeable substance is only slight, and if also the exchange of the impermeable substance through the membrane is delayed in relation to the exchange of the permeable substance, so that during the exchange of the permeable substance, no significant exchange of the impermeagle substance takes place, i.e., if the rate constant $k_s$ for the permeable substance is sufficiently great compared to that of the impermeable substance, i.e., if during the test, practically none of the impermeable substance gets through the membrane. On the other hand, that means that with the specified membrane, a substance is to be considered permeable if, during the execution of the process, it is sufficiently delayed in relation to the pure solvent, but still gets through the membrane relatively rapidly in relation to the impermeable substance. Accordingly, a substance is to be considered impermeable if, during the execution of the process, practically none gets through the membrane. In this sense, accordingly, a material can even be practically impermeable, although the reflection coefficient $\sigma_s < 1$, if its permeability (i.e., $k_s$) in the membrane is sufficiently low.

In the processes of the prior art, to establish the working pressure $P_O$ in the osmotic cell, a solution is used as an osmometer solution in which there is an impermeable substance, so that as a result of the osmotic pressure difference across the membrane, the hydrostatic working pressure $P_O$ builds up in the osmotic cell.

The exchange of the solution to be tested and the solvent must take place very rapidly in comparison to the half-life for the flow of the pure solvent through the membrane, which can be in the range of seconds.

In the execution of the alternative prior art Process Ib, compared to the first Process Ia, the time $t_{min}$ must also be determined from the beginning of the exchange process of the two solutions (solvent and solution to be tested) until the establishment of the minimum pressure $P_{min}$ and the rate constant $k_s$ for the pressure increase which occurs following the minimum pressure, which is a consequence of the permeation of the permeable substance through the membrane. Before the execution of Process Ib, the reflection coefficient $\sigma_s$, which is a material constant with a given membrane and a given solvent, must also be determined in the manner of the prior art.

A process known as Process II is also described in U.S. Pat. No. 4,706,495, which corresponds to German Laid Open Patent Appln. No. DE-OS 35 25 668, which consists of the Process Variants IIa, and IIb. In this prior art process, after the exchange of the solvent and the solution to be tested, which contains two substances, the initial slope $(dP/dt)_{t=0}$ of the pressure/time curve is measured from the pressure decrease in the osmotic cell, and with this value, according to calibrated values or from the equation $$(dP/dt)_{t=0} = -\frac{A_o}{V_o} \cdot Lp \cdot \epsilon \cdot RT(\sigma_1 \cdot C_1 + \sigma_2 \cdot C_2) \quad (5)$$

the result $$X_1 = \sigma_1 \cdot C_1 + \sigma_2 \cdot C_2 \quad (6)$$

is determined.

In these equations:
$A_o$ is the effective surface of the membrane,
$V_o$ is the volume of the osmotic cell,
$Lp$ is the hydraulic conductivity of the membrane,
$\epsilon$ is the modulus of volume elasticity of the osmotic cell,
$R = 8.31434$ J/° K. mol,
$T$ = absolute temperature,
$\sigma_1$ = reflection coefficient of the substance 1,
$C_1$ = the concentration of the substance 1,
$\sigma_2$ = the reflection coefficient of the substance 2, and
$C_2$ = the concentration of the substance 2.

According to the Process Variant IIa, simultaneous with the determination of the result $X_1$, according to the process described, another measurement is performed using a second osmotic cell with a membrane having a different retention (or rejection) capacity for the substance, whereby another result $$X_2 \sigma_1' \cdot C_1 \sigma_2' \cdot C_2 \quad (7)$$

is determined, and then, by means of the two results $X_1$ and $X_2$, the concentration of the two substances is calculated. According to the Process Variant IIb, the additional measurement is executed by means of the second osmotic cell according to one of the Process Ia or Ib, whereby a membrane is used which has a retention capacity for the substance such that, in relation to the membrane used, the one substance is permeable and the other substance is impermeable, and whereby it is sufficient for only the concentration of the permeable or the concentration of the impermeable substance to be determined, and using the result $X_1$, the concentration of both substances can be calculated.

For the execution of the Process Variant IIa, according to which the result $X_1$ and simultaneously the result $X_2$ are determined, it must be guaranteed that the time constants of the osmotic cells are sufficiently low. "Sufficiently low" means, for example, if a blending process is being observed, that the time constant of the blending process is high compared to that of the mixing process in the osmotic cell. This is the case if the K-values of the osmotic cells $$K = \frac{A_o}{V_o} \cdot Lp \cdot \epsilon \cdot RT \quad (8)$$

are sufficiently high. This can be achieved by the selection of suitable osmotic cells, since it is a question with the factors $A_o/V_o$, $Lp$ and $\epsilon$ of structurally specific values of an osmotic cell or its membrane. On the other hand, the initially linear course of the pressure/time curve which is established as the result of a change in concentration, compared to the duration of the mixing phase which takes place during the exchange of two solutions in the measurement system, must be sufficiently long.

The reflection coefficients $\sigma_1$ and $\sigma_2$ must be determined in advance. For the determination of $\sigma_1$ and $\sigma_2$, the initial slope caused by substance 1 or 2 of known concentration is compared to that obtained after the addition of a known concentration of an impermeable substance.

In Process Variant IIa, the membranes of the two osmotic cells are selected so that the values for $\sigma_1$ and $\sigma_1'$ and $\sigma_2$ and $\sigma_2'$ differ sufficiently.

The constant value K for a specified osmotic cell is determined by calibration.

The short-term mixing of the solutions which occurs during the exchange of solutions in a vessel or in a pipeline can lead to a situation where the initial pressure decrease in the osmotic cell is imprecisely defined. Only when the solutions have been completely exchanged, is the linear course of the pressure/time curve established, from which then, during the execution of Process II, the initial slope is determined.

The Process Variant IIa makes possible a more rapid determination of the concentrations of the two substances than do Processes Ia and Ib, since in the latter, the path of the entire pressure curve must be watched until the final value $P_E$ is achieved. For this purpose, however, the execution of Process IIa (and Process IIb) requires the use of two osmotic cells; the execution of Process Ia or Ib, however, requires only one osmotic cell for either process.

With Process IIb, too, according to which the simultaneous measurement is made via the determination of the pressure difference $(P_E - P_{min})$ or $(P_O - P_e)$, a more rapid determination of the concentration of a substance is possible if the concentration of one of the substances is constant, and only the concentration of the other substance is to be measured.

Of course, even if it is not primarily a question of the determination of the concentration of the substances, but of the determination of the time of the change in concentration in a solution in a vessel or a tube, Process II can be conducted without a simultaneous measurement, i.e., the pressure decrease in the osmotic cell is determined by means of only one osmotic cell. In this manner, one osmotic cell can be used as a control or alarm device.

Applications for the determination of the concentration of substances include, in particular, the determination of low-molecular, permeable substances and high-molecular, impermeable substances. One application, for example, is the determination of the concentration of (permeable) alcohol and (impermeable) sugar during alcoholic fermentation. Such a determination is significant both for the production of alcoholic beverages and also for the production of industrial alcohol. The processes of the prior art are also useful for the determination of blood alcohol concentration in human beings.

Other applications are the determination of the concentration of organic solvents in aqueous solutions (e.g., of ethanol methanol, propanel, esters, ethers, acetone, etc.) as they occur in certain chemical processes. Another area of application in the chemical industry is the determination of solvent residues, salts and other pollutants in waste waters.

The processes of the prior art can also be used in the monitoring of dialysis processes.

A special application for the prior art Process II is in the rapid recognition of a change in a solution, such as occurs in a brewery or in other sectors of the food and beverage industry when there is a change between a purification agent (e.g., water) and a product (e.g., beer).

By means of the rapid determination of the time of the solution change at a given point, product losses can be strictly limited. Process II can also be used in connection with only one single osmotic cell as an alarm system, e.g., to detect leaks in tanks, pipelines, etc. on account of its ability to recognize rapid changes in concentration.

Therefore, there are many applications of the known processes. One disadvantage of these known processes, however, is that, for example, high concentrations of substances can only be measured with a relatively limited precision.

OBJECT OF THE INVENTION

The object of the invention is to improve the known processes so that with the improved process, the concentrations of substances present in high concentration can also be determined with greater absolute precision, e.g., in the range of 0.01 wt %.

SUMMARY OF THE INVENTION

This object is achieved by the invention in that, for the precise determination of the concentration of the substances, the reference solution and the osmometer solutions are selected so that to establish a working pressure $P_O$, an excess of impermeable substance is contained in the osmometer solution compared to the reference solution of not more than 80 mOsm, that the osmometer solution contains the substances to be determined, whereby the difference in the concentrations of the substances in the osmometer solution and in the solution to be tested is not more than 70 mOsm, and that the total concentration of the substances in the solution to be tested is determined on the basis of the concentration of the substances in the osmometer solution.

In the process according to the invention, in contrast to the processes of the prior art, difference measurements of the osmotic pressure of the permeable and impermeable substance are conducted, whereby particularly sensitive pressure sensors can be used for the pressure measurement. Since the reference solution contains the substances whose concentration is to be determined in a concentration which is already comparable to that of the solution to be tested, the concentrations of the substances on both sides of the membrane cancel out their osmotic effect on one another, and the osmotic cell "sees", to a certain extent, only differences in the concentration of the substances. The absolute level of the working pressure $P_O$ under these conditions results from the concentration of the additional impermeable substance contained in the cell.

For the implementation of the measures proposed by the invention in Processes Ia and Ib, $P_O - P_E$ gives the difference in the concentration (concentration of the impermeable substance or substances) and $P_E - P_{min}$ gives the difference in the concentration of the permeable substance. Taking into consideration the specified concentration of the substances in the reference solution, the total concentration of the substances can thereby be determined with great precision.

In a variation of the known Process I, $P_O - P_E$ can be determined from the change of dP/dt in the minimum. When this process is executed, too, as a result of the use of the measures proposed by the invention, the precision of the determination of $(d^2P/dt^2)_{min}$ is increased.

According to Process Ia, the difference concentrations are determined from the initial slope $(dP/dt)_{t=0}$, and $P_e$ is determined separately. When two reference solutions with different concentration ratios of permeable to impermeable substance are used, the concentrations can be determined by two measurements of the initial slopes, whereby the reflection coefficients must be determined in advance.

A particularly advantageous process variant according to the invention is that, for the determination of small deviations of the concentrations of substances in a solution from a specified concentration, a solution with the specified concentration is used as the reference solution, and solution with the specified concentration of substances plus the excess impermeable substances is used as the osmometer solution.

This process variant makes it possible, in particular on the basis of Process IIa, i.e., the determination of the concentrations by means of the initial slope, to quickly measure and regulate the concentration of solutions (or of waste water) in tanks, pipelines, etc. if the specified concentration is used as the reference solution.

When the process described by the invention is used, the transient pressure changes during the change from the reference solution to the solution to be tested are accordingly small, so that a high-resolution pressure sensor can be used. Under these conditions, however, a precise measurement requires a sufficiently constant temperature during the measurements. In particular, if the deviation of the concentrations of substances of less than 20 mOsm is to be determined, the temperature of the solutions at the measurement point must be kept constant.

In addition to the applications described above, the invention can be used generally for the determination of small concentrations of a substance or high concentrations of foreign substances, e.g., for the determination of blood alcohol concentration. Other applications are the precision control of concentrations in various sectors of the chemical and pharmaceutical industry, as well as biotechnology and the food and beverage industry.

A suitable apparatus for the execution of the various processes according to the invention is one which has at least one vessel and at least one measurement head (measurement head "A"), which consists of an osmotic cell with a pressure measurement apparatus, which has a rigid metal or plastic wall and whose membrane has the highest possible modulus of elasticity, the highest possible conductivity for the solvent and a sufficient retention capacity for the substances in the solution to be tested. The ratio of the volume of the osmotic cell to the effective surface of the membrane is a maximum of 0.2 mm. The measurement head or heads can be immersed in the vessel, whereby the vessel can be optionally filled with a solution (reference solution) to establish the working pressure $P_O$, with the solution to be tested and, if necessary, with standard solutions. This apparatus according to the invention is characterized by an apparatus which is used to keep the temperature of the solutions at the measurement point constant. In the simplest case, this can be a thermostat, where the measurement point is located in a temperature-controlled enclosure.

In one advantageous embodiment of the apparatus according to the invention, there are closable feed and discharge lines on the osmotic cell for the osmometer solution.

The apparatus is also suitable for the execution of the various processes according to the invention, in that it exhibits the storage containers and at least one measurement head (measurement head "B"), which consists of an osmotic cell with a pressure measurement apparatus and a vessel, whereby the osmotic cell has a rigid metal or plastic wall and the membrane of the cell exhibits the greatest possible conductivity for the solvent and a sufficient retention capacity for the substances in the solution to be tested. The ratio of the volume of the osmotic cell to the effective surface of the membrane is again a maximum 0.2 mm. The vessel is in communication via the most rigid possible membrane with the osmotic cell, and is equipped with a feed and discharge line for the solution (reference solution) to establish the working pressure $P_O$, for the solution to be tested and, if necessary, for a standard solution. The feed and discharge line of the vessel as well as the inside of the container are designed so that the solutions fed into them can be filled into the vessel as rapidly as possible. Storage vessels for the solution used to establish the working pressure $P_O$ (i.e., the reference solution) are in communication with the feed line for the vessel of the measurement head or heads. There is also a recipient or a pipeline containing the solution to be tested which is in communication with the feed line for the vessel of the measurement head or heads. This apparatus according to the invention is also characterized by an apparatus used to keep the temperature of the solutions at the measurement point constant.

The devices can be configured, regardless of the type of measurement head used and the type of process used, either as a portable measurement apparatus or as a piece of fixed equipment, e.g., as part of an installation for the execution of a given process, such as alcoholic fermentation. It may be appropriate to have a control apparatus to control automatic operation of the apparatus, whereby in alternations at specified intervals of time, the solution used to establish the working pressure $P_O$ and the solution to be tested are filled into the vessel of the measurement head "B" or into the vessel to which the measurement head "A" is attached.

If there are two measurement heads to execute the Process II, then of course, a measurement head "A" and a measurement head "B" can also be used.

Moreover, a very advantageous apparatus is one in which there is additional control and/or monitoring equipment, which picks up the electrical output signals of the measurement head ("A", "B") or - when Process II is used - of the measurement heads ("A", "A" or "A", "B" or "B", "B"), and which is used to control and/or monitor processes which take place as a function of the concentration of the substances tested. In addition to a monitoring of the processes, certain specified concentrations of the substances can be electronically regulated in such processes. Such processes include, for example, alcoholic fermentation, in which the concentration of alcohol (permeable) and the concentration of sugar (impermeable) gives an idea on the status of the fermentation, or the monitoring of solvent concentrations in waste water. When the process according to the invention is used, conventional analytical concentration determinations are unnecessary. The frequency with which the measurement can be repeated, in the case of the application of Processes Ia and Ib, is a function, on one hand, of the test time, which can amount to several minutes, and on the other hand, of the process itself which is being monitored. The test time is a function of the physical characteristics of the membrane (conductivity for the solvent and the dissolved substances) and of the measurement head ("A", "B") (Volume/surface ratio of the osmotic cell, modulus of elasticity of the volume), and can therefore be adjusted to suit the measurement problem at hand.

Embodiments of the measurement head ("A", "B"), and embodiments of the apparatus according to the invention, are illustrated schematically in the accompanying drawings, and are explained in greater detail below.

The accompanying drawings also include calibration diagrams for the illustrated embodiments of the invention.

BRIEF DESCRIPTION OF THE DRAWINGS

FIGS. 1–4 illustrate the prior art. Thus:

FIG. 2 shows a measurement head "A", consisting of an osmotic cell with a pressure measurement apparatus installed on an installation which contains the solution to be measured;

FIG. 4 shows an apparatus with measurement head "B" according to FIG. 3 with automatic control of the measurement process as well as a process control;

FIGS. 5–13 illustrate the present invention. Thus:

FIG. 5 shows a measurement head "A", consisting of an osmotic cell with pressure measurement equipment, as well as a micrometer screw with a precision control rod;

FIG. 6 shows an apparatus with a measurement head "A", consisting of an osmotic cell with a pressure measurement device;

FIG. 7 shows a measurement head "B", consisting of an osmotic cell and a vessel adjacent to the cell;

FIG. 8 shows an apparatus with measurement head "B" as shown in FIG. 7 with automatic control of the measurement process, as well as a process control;

FIG. 9 shows the pressure curve in the osmotic cell during the measurement process; and FIGS. 10–13 are calibration diagrams (Process Ia) corresponding to Embodiments 1–3.

DESCRIPTION OF THE PREFERRED EMBODIMENTS

The prior art illustrated in FIGS. 1–4 will first be described, after which the present invention illustrated in FIGS. 5–13 will be described.

Figure 1A:
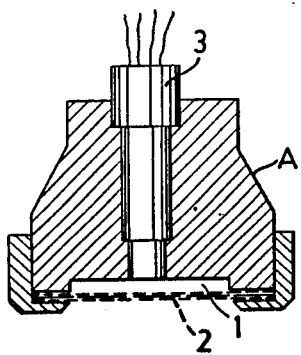
FIG. 1A shows a measurement head "A", consisting of an osmotic cell with a pressure measurement apparatus.
Figure 1B:
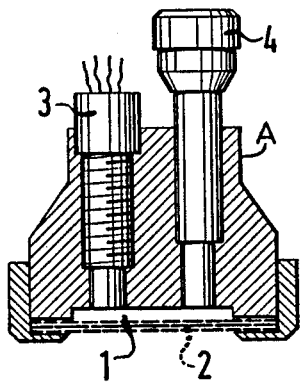
FIG. 1B shows a measurement head "A", consisting of an osmotic cell with a pressure measurement apparatus, as well as a micrometer screw with a control rod.

The measurement head "A" illustrated in FIG. 1 comprises an osmotic cell 1 with a rigid partition of metal or plastic, with a membrane 2 which at least partly forms its outer boundary, and a pressure measurement apparatus 3 with a pressure transducer which emits electrical signals. An example of such a pressure transducer is found in U.S. Pat. No. 4,413,528, issued on Nov. 8, 1983, which is incorporated herein by reference. The membrane 2 used for the measuring head was obtained from REICHELT CHEMIETECHNIK, Heidelberg, Federal Republic of Germany, under the tradename "THOMAPOR Reverse Osmosis Membranes." A manufacturer for asymmetrical membrane foils used for reverse osmosis processes is the KALLE Company, a subsidiary of HOECHST AG, Wiesbaden, Federal Republic of Germany, under the tradename "NADIR Separation Foils for Hyperfiltration". The foils consist of a laminate of membrane-forming agent and the backing material, such a paper, polyester fleece, or polypropylene fleece. A metal grid can be disposed on the membrane 2 on the side of the membrane facing away from the osmotic cell 1. Additionally, the membrane 2 can, for example, comprise a hollow fiber acting as a hyperfiltration membrane. There is also an apparatus 4 for the controlled volume change of the osmotic cell 1, comprising a micrometer screw with control rod, by means of which a measurable volume change of the osmotic cell can be made. This controlled volume change, which results in a change in pressure in the osmotic cell, can therefore be used to check the rigidity of the osmotic cell via the pressure measurement apparatus 3 or to determine the modulus of elasticity of the cell. The osmotic cell 1 can also be equipped with an agitation device, such as a magnetic stirrer of the type comprising a small magnet or metallic object disposed within the osmotic cell and manipulated by a rotating magnetic field generated external to the osmotic cell. Such stirrers are known in the art, and are not illustrated herein. Examples of such magnetic stirrers are described in U.S. Pat. Nos. 4,534,656; 4,512,666; 4,498,785; 4,465,377; 4,227,815: 4,162,855; and 4,080,663, which patents are incorporated herein by reference.

Figure 2:
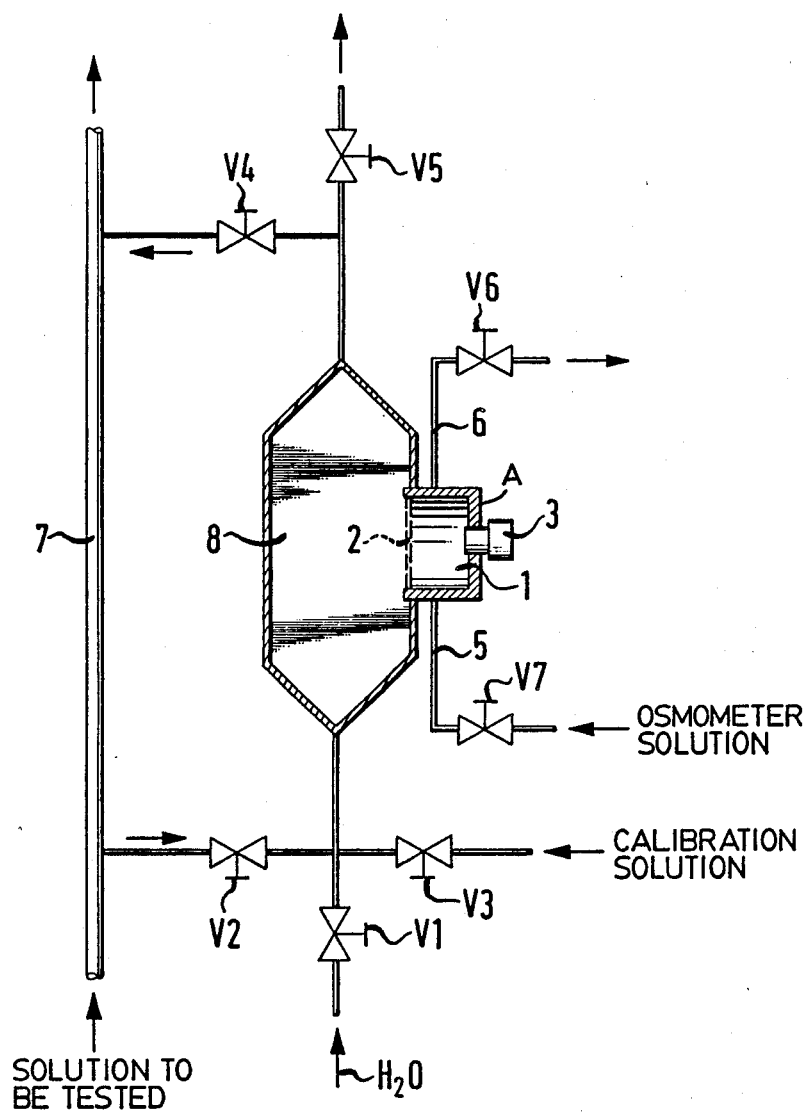

FIG. 2 shows a measurement head "A" of the type illustrated in FIG. 1, comprising an osmotic cell 1 and a pressure measurement apparatus 3 in use. An apparatus for the controlled volume change is not present in this embodiment, but there is a closable feed line 5 and a closable discharge line 6 for the osmometer solution.

For the determination of the concentration of dissolved substance in a solution in the line 7, first of all a solution suitable for the establishment of the working pressure $P_O$, e.g. distilled water, is admitted via open valves V1 and V5 and closed valves V2, V3 and V4 into a container 8, whereby the solution ($H_2O$) is brought into communication via a membrane 2 with the osmometer solution, which is in the osmotic cell 1. After the establishment and determination of the working pressure $P_O$, the solution to be tested is then admitted to the container 8 via open valves V2 and V4 or V5 and closed valves V1, V3 and possibly V5 or V4, whereupon the minimum pressure $P_{min}$ is established first of all, and then the final pressure $P_E$ During this measurement process, of course, the valves V6 and V7 are closed. For calibration, if necessary, a calibration solution can be admitted to the container 8 via the valve V3, with an appropriate setting of the other valves.

Figure 3A:
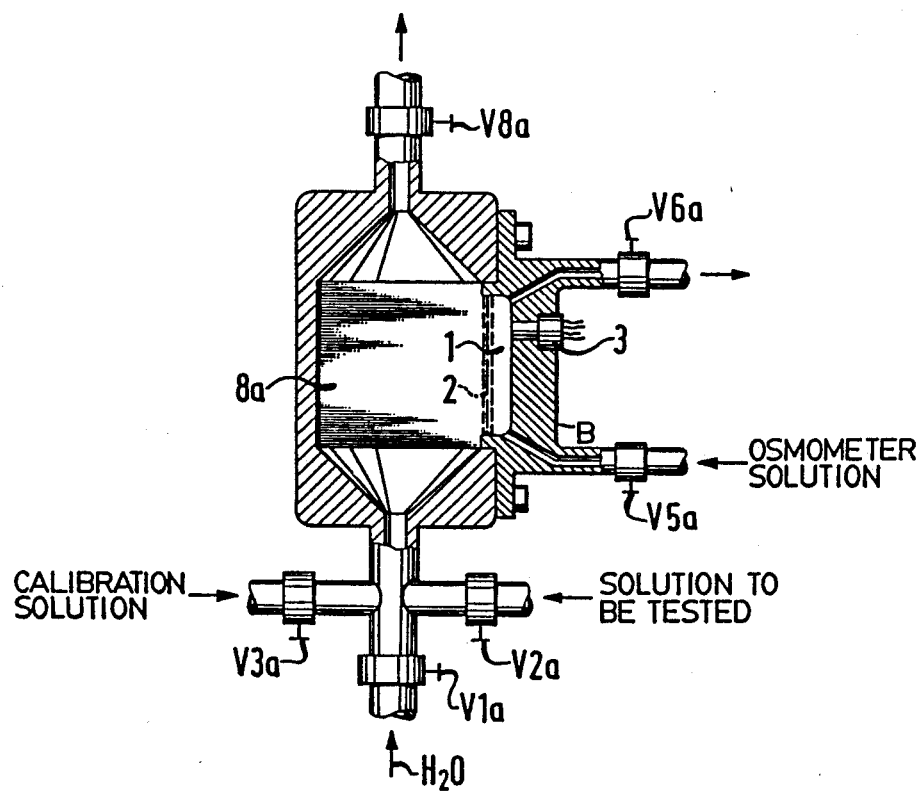
FIG. 3A shows a measurement head "B", consisting of an osmotic cell and a container adjacent to the cell.
Figure 3B:
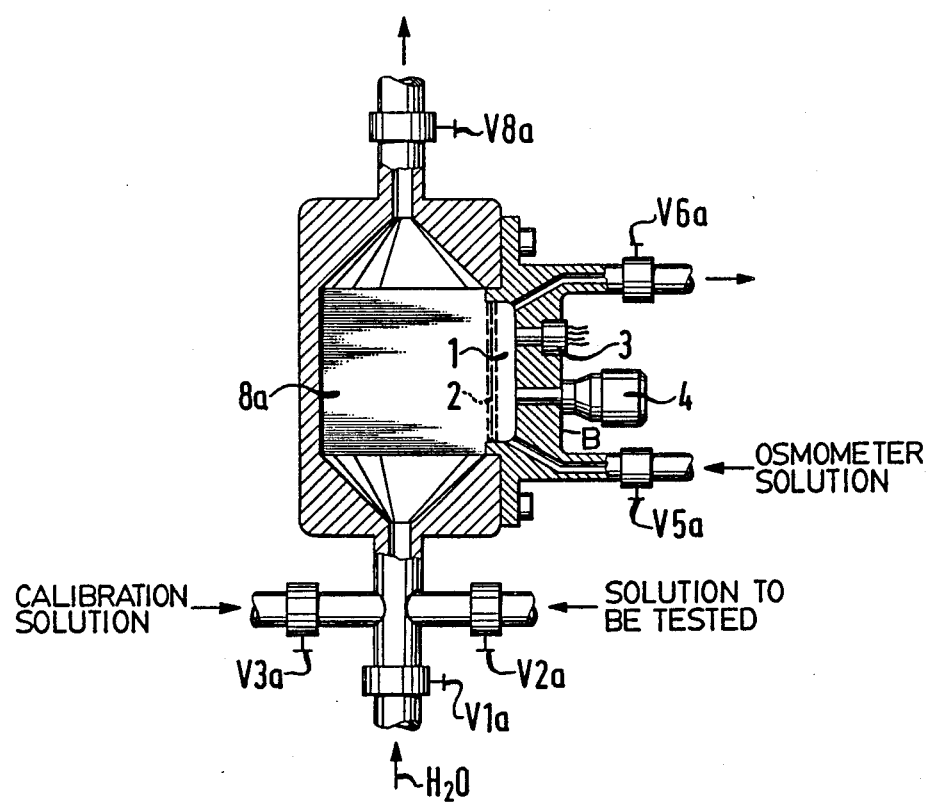
FIG. 3B shows a measurement head "B", consisting of an osmotic cell and a container adjacent to the cell, as well as a micrometer screw with a control rod.

FIG. 3 shows a measurement head "B" with an osmotic cell 1 and a membrane 2, containing a container 8a corresponding to the container 8 in FIG. 2. The valves V1a, V2a, V3a, V5a and V6a correspond to the valves V1, V2, V3, V5 and V6 represented in FIG. 2. V8a is the outlet valve of the container 8a integrated into the measurement head. For the measurement head illustrated in FIG. 3, there is also a pressure measurement apparatus 3 with an electrical indicator, as well as an apparatus 4 for the controlled volume change of the osmotic cell 1 as described above in connection with measurement head "A" of FIGS. 1 and 2. Moreover, the several features described in combination with measurement head "A" can also be used in the measurement head "B" shown in FIGS. 3 and 4.

Figure 4:
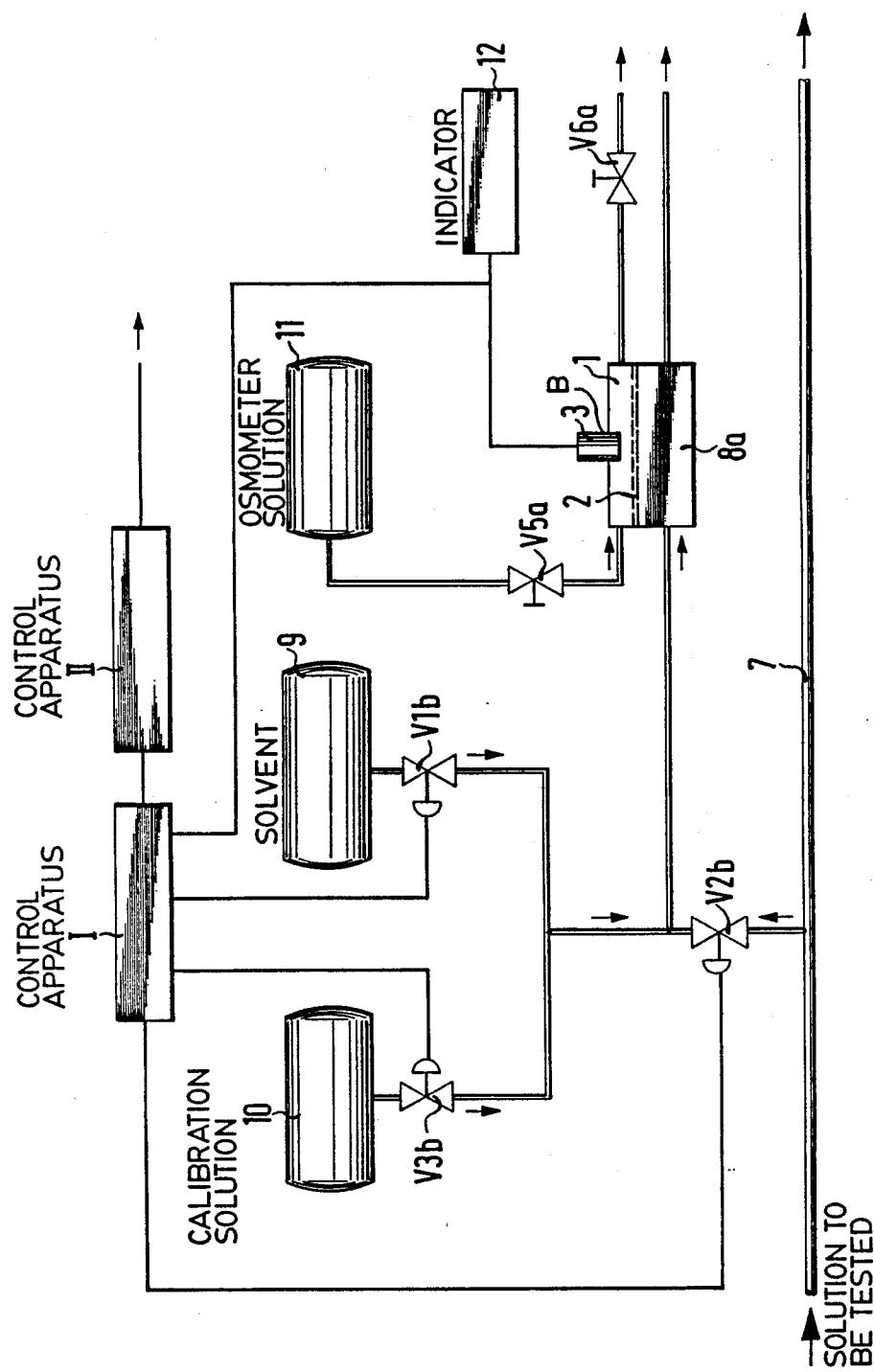

FIG. 4 shows an apparatus with a measurement head "B" of the type illustrated in FIG. 3, which is suitable for the determination of the concentration of substances in a solution flowing in line 7. The valves V1b, V2b and V3b correspond functionally with the valves V1a, V2a and V3a illustrated in FIG. 3, but they are designed as remote-control cutoff valves, which are electrically connected to the control apparatus I. By means of this control apparatus I, at pre-determined time intervals, solvent is fed in from the storage container 9 via the valve V1b (with valves V2b and V3b closed) into the container 8a to set the working pressure $P_O$, and then the solution to be tested is introduced from the line 7 via the valve V2b (with valves V1b and V3b closed). In addition, at longer time intervals, by means of the control apparatus I, the feed of calibration solutions can be tripped from the storage container 10 via the valve V3b (with valves V1b and V2b closed) into the container 8a. There is also a storage container 11 for the osmometer solution.

As also shown in FIG. 4, the electrical output signals from the pressure measurement apparatus 3 are displayed on an indicator 12 and taken over by the control apparatus I. By means of a control apparatus II, which is electrically connected to the control apparatus I, the process is controlled as a function of the measurement values determined.

Alternative processes are possible which will be described in detail hereinafter.

There is first described a method identified as Method Ia below. This method consists of the use of the most rigid possible osmotic cell, as well as a membrane which exhibits the highest possible conductivity for the solvent and a sufficient retaining capability for the substances, and that, first of all, using a suitable solution brought into communication with the osmometer solution via the membrane as well as a suitable osmometer solution, a work pressure $P_O$ is established and determined, whereupon the solution brought into communication with the osmometer solution via the membrane is replaced sufficiently rapidly by the solution containing the substances, whereupon the minimum pressure $P_{min}$ established in the osmotic cell is determined, as well as the final pressure $P_E$ established in the osmotic cell after the subsequent pressure increase, whereby, on the basis of calibrated values, the concentration of the impermeable substance or substances in the solution to be tested is computed from the pressure difference $P_O - P_E$ and the concentration of the permeable substance in the solution from the pressure difference $P_E - P_{min}$. The process can be conducted so that the concentration of impermeable ($C_{imp}^o$) substances and permeable ($C_s^o$) substances in the solution to be is determined by calibration of the measurement system with various solutions containing impermeable and permeable substances in different known concentrations, whereby care is to be taken in the determination of the permeable components that the calibration solutions contain the impermeable substance in approximately the same concentration as the solution to be tested, whereupon their concentration of permeable substance results from the graph $(P_E - P_{min}) = f(C_2^o)$ and the concentration of impermeable substances from the graph $(P_O - P_E) = g(C_{imp}^o)$. $(P_O - P_E) = g(C_{imp}^o)$ represents in each case a straight line, while $(P_E - P_{min}) = f(C_s^o)$ can deviate from the linear form, since $t_{min}$ is a function of the mixing ratio $\sigma_s \cdot C_s^o / C_{imp}^o$.

There is next described an alternative method identified as Method Ib. The method consists of using an osmotic cell which is as rigid as possible, and a membrane, which exhibits the highest possible conductivity for the solvent and a sufficient retention capability for the substances, and that first of all, using a suitable solution brought into communication via the membrane with the osmometer solution and a suitable osmometer solution, a working pressure $P_O$ is established, whereupon the solution brought into communication with the osmometer solution via the membrane is replaced sufficiently rapidly by the solution containing the substances, whereupon the minimum pressure $P_{min}$ established in the osmotic cell, the time $t_{min}$, within which the minimum pressure $P_{min}$ is achieved, the velocity constant $k_s$ for the exponential pressure increase after the minimum pressure, and the final pressure $P_E$ which is achieved after the pressure increase are determined, after which the concentration $C_s^o$ of the permeable substance can be computed from the equation:

$$P_E - P_{min} = \sigma_s RT C_s^o \cdot \exp(-k_s t_{min}) \qquad (1)$$

with R = 8.31434 J/°K. mol;
T = absolute temperature; and
$\sigma_s$ = reflection coefficient of s,
and the concentration ) of the impermeable substance or substances is determined from the equation:

$$P_O - P_E = RT \cdot C_{mp}^o \qquad (2)$$

The osmotic cell to be used should be as rigid as possible, that is, an osmotic cell with a rigid wall and rigid membrane, so that during the execution of the process, the change of the volume of the osmotic cell is negligible. For this case, Equations 1 and 2 apply.

For the case, however, in which the membrane and the osmotic cell are not sufficiently rigid and the changes in the volume of the osmotic cell which occur during the determination are not negligible, the volumetric elastic modulus ($\epsilon = V(\Delta P/\Delta V)$) can be determined by means of a suitable apparatus, after which the concentration $C_s^o$ of the permeable substance can be obtained from the equation:

$$P_E - P_{min} = \frac{\epsilon}{\epsilon + RT \cdot C_{imp}^i} \cdot \sigma_s \cdot RT \cdot C^o_s \cdot \exp(-k_s \cdot t_{min}) \qquad (3)$$

and the concentration $C_{imp}^o$ of the impermeable substance from the equation:

$$P_0 - P_E = \frac{\epsilon}{\epsilon + RT \cdot C_{imp}^i} RT \cdot C^o_{imp} \qquad (4)$$

The membrane to be used in both Methods Ia and Ib should exhibit the highest possible conductivity for the solvent and a sufficiently high retention capability for the substances or solutes of interest. The retention capability of the membrane is sufficient for the substances, if the exchange of the permeable substance through the membrane is delayed in relation to the exchange of the pure solvent via the membrane, so that during the exchange phase of the pure solvent, the exchange of the permeable substance is only minor. Moreover, if the exchange of the impermeable substance is delayed in relation to the exchange of the permeable substances so that during the exchange of the permeable substance, no notable exchange of the impermeable substance takes place. That is, if the velocity constant $k_s$ for the permeable substance is sufficiently large compared to that of the impermeable substance or if during the test practically no impermeable substance gets through the membrane. On the other hand, with the specified membrane, a substance is to be considered permeable if it is sufficiently delayed during the execution of the method in relation to the pure solvent, but gets through the membrane sufficiently rapidly in relation to the impermeable substance. Accordingly, a substance is to be considered impermeable if, during the performance of the method, practically none of it gets through the membrane. In this sense, accordingly, a substance can be practically impermeable, although the reflection coefficient $\sigma_s$ is less than 1, if its permeability ($k_s$) in the membrane is sufficiently low.

To set the working pressure $P_O$, a suitable osmometer solution is introduced into the osmotic cell, and a suitable solution is brought into communication with the osmotic cell via the membrane. The pure solvent (e.g. water) is suitable for use as the solution outside the osmotic cell. A suitable osmometer solution, on the other hand, is a solution in which there is an impermeable substance, so that as a result of the osmotic pressure difference across the membrane in the osmotic cell, the hydrostatic working pressure $P_O$ builds up. The concentration of the impermeable substance in the osmometer solution is thereby selected appropriately, i.e. a working pressure $P_O$ is to be selected so that in the subsequent determination of the substances, properly measurable differential pressures ($P_O - P_E$) or ($P_E - P_{min}$) are obtained.

After the determination of the working pressure $P_O$ in the osmotic cell, the solution placed in communication with the osmotic solution via the membrane, e.g. the pure solvent, is replaced sufficiently rapidly by the solution containing the substances to be determined, whereupon the minimum pressure $P_{min}$ is established. Since this minimum pressure is determined by the concentration of the permeable substance in the solution (resulting from $P_E - P_{min}$), the replacement process of the two solutions must take place very rapidly in relation to the half-value time for the flow of the pure solvent through the membrane, which can be in the range of seconds.

In the performance of the alternative Method Ib, in relation to the first Method Ia, the time $t_{min}$ from the beginning of the replacement process of the two solutions (solvent and solution to be tested) until the establishment of the minimum pressure $P_{min}$ must also be determined, as must the velocity constant $k_s$ for the pressure increase which takes place after the minimum pressure, which is a result of the permeation of the permeable substance through the membrane. Before the execution of Method Ib, in addition, the reflection coefficient $\sigma_s$, which is a material constant with a given membrane and a given solvent, must be determined. This is done by using calibration solutions indicated in the process described by E. Steudle and S. D. Tyerman (1983), "Determination of permeability coefficients, reflection coefficients and hydraulic conductivity of *Chara corallina* under the pressure probe: Effects of Solute Concentration", J. Membrane Biol. 75 85–96, the contents of which are incorporated herein by reference.

After that, the osmotic cell is initially placed in communication with the pure solvent, whereby the working pressure $P_O$ is established. Then a solution is applied, which contains only the permeable substance in a known concentration From the pressure difference ($P_O - P_{min}$), $\sigma_s$ results after a correction for the flow of the permeable substance.

If the solution to be tested contains only one each impermeable and permeable substance, when Methods Ia and Ib are applied, the absolute concentration of these substances can either be determined by using calibration values or according to the above-mentioned equations If a single permeable substance, but more than one impermeable substance, is contained in the solution, the concentration of the permeable substance and the total concentration of the impermeable substance is determined. If, in addition to the impermeable substance or substances, there are several permeable substances in the solution, then this has no influence on the determination of the (total) concentration of the impermeable substance or substances from the difference $P_O - P_E$.

The methods indicated can therefore be applied to solutions with very different substances dissolved in them. The selection of an appropriate membrane can be made by regarding certain substances in the solution as impermeable and others as permeable, in the sense of the definitions described above. A particular version of Methods Ia and Ib consists of computing the rate constant $k_s$ for the exponential pressure increase which occurs following the minimum pressure and the temporal change $(d^2P/dt^2)^{min}$ of the slope of pressure/time curves around the pressure minimum, and calculating the final pressure $P_E$ from the equation:

$$k_s \cdot k_w = \frac{1}{P_E - P_{min}} (d^2P/dt^2)_{min} \quad (4a)$$

whereby previously, for the osmotic cell (1) used, the rate constant $k_w$ has been computed for the pressure change up to the minimum.

The rate constant $k_w$ is a measure for the rate of water exchange through the membrane. $k_w$ can be measured from pressure/time curves using a solution which only contains an impermeable substance.

When the above-mentioned alternative methods of Ia and Ib are carried out, then $(d^2P/dt^2)_{min}$ can be determined graphically or by curve fitting by means of a computer. The latter method is preferable because it can be carried out more rapidly.

In another configuration of the above-mentioned method variants, the rate constant $k_s$ is determined in advance for the solution to be tested and containing the substances. When the alternative methods are subsequently executed, the previously determined value for $k_s$ (likewise the one for $k_w$) is only used for the calculation of $P_E$ in the determination (4a). This has the advantage that the determination of the concentrations can be made in a shorter period of time, since for this purpose, only the course of the pressure curve up to the end of the area needed for the determination of $(d^2P/dt^2)_{min}$ around the minimum must be used. This can lead to significantly shorter measurement times, since the exponential increase of the pressure curve which takes place just after the minimum is relatively the longest portion of the pressure curve.

Another alternative method is described below and identified as Method II, which consists of the alternative Methods IIa and IIb. This process requires the most rigid possible osmotic cell, as well as a membrane with the greatest possible conductivity for the solvent and the greatest possible retaining capacity for the substances. Initially, using a suitable solution brought into communication with the osmometer solution via the membrane and a suitable osmometer solution, a working pressure $P_O$ is established. Whereupon, if the solution to be tested contains two substances, after replacement of the solution brought into communication with the osmometer solution via the membrane by the solution containing the two substances, from the pressure drop in the osmotic cell which occurs because of this replacement in this osmotic cell, the initial slope $(dP/dt)_{t=0}$ of the pressure time curve is determined, and with this measurement, based on calibration values or values from the equation:

$$(dP/dt)_{t=0} = -\frac{A_o}{V_o} \cdot Lp \cdot \epsilon \cdot RT(\sigma_1 \cdot C_1 + \sigma_2 \cdot C_2) \quad (5)$$

the result $$X_1 = \sigma_1.C_1 + \sigma_2.C_2 \quad (61)$$

is determined, whereby:
 $A_o$ is the effective surface area of the membrane;
 $V_o$ is the volume of the osmotic cell;
 Lp is the hydraulic conductivity of the membrane;
 $\epsilon$ is the volumetric elastic modulus of the osmotic cell;
 R = 8.31434 J/°K. mol;
 T is the absolute temperature;
 $\sigma_1$ is the reflection coefficient of the substance No. 1;
 $C_1$ is the concentration of the substance No. 1;
 $\sigma_2$ is the reflection coefficient of the substance No. 2; and
 $C_2$ is the concentration of substance No. 2, and that parallel to the determination of the resultant value $X_1$, according to the described method, another measurement is made by means of a second osmotic cell with a membrane with another retaining capability for the substances (Method IIa), whereby another result $$X_2 = \sigma_1'.C_1 + \sigma_2'C_2 \quad (&7)$$

is determined. The concentrations of the two substances are then computed by means of the two result values $X_1$ and $X_2$, or the other measurement is conducted by means of the second osmotic cell according to one of the Methods Ia or Ib, whereby a membrane with appropriate rejection properties for the substances is used so that, with regard to the membrane used, the one substance is permeable and the other substance is impermeable, and whereby it is sufficient that only the concentration of the permeable substance or the concentration of the impermeable substance be determined, and using the result $X_1$, the concentrations of both substances are calculated (Method IIb).

For the execution of the alternative Method IIa, according to which the resulting value $X_1$ and simultaneously the resulting value $X_2$ are determined, it must be guaranteed that the response times (time constants) of the osmotic cells are sufficiently small in relation to the time constant of the process to be observed That is the case when the K-values of the osmotic cells:

$$K = \frac{A_o}{V_o} \cdot Lp \cdot \epsilon \cdot RT \quad (8)$$

are sufficiently large. Since with regard to the factors $A_o/V_o$, Lp and $\epsilon$, it is a question of design-specific values of an osmotic cell or its membrane, it can be achieved by the selection of suitable osmotic cells. On the other hand, the practically linear course of the pressure/time curve, for sufficiently short times after a change of solutions, should be sufficiently long compared with the duration of the mixed phase, which is formed during the exchange of the two solutions in the measuring system.

The reflection coefficients $v_1$ and $\sigma_2$ are to be determined in advance. For the determination of $\sigma_1$ or $\sigma_2$, the initial slope which the substance No. 1 or 2 of known concentration causes is compared with that which is obtained after the addition of an impermeable substance (in known concentration). In alternative Method IIa, the membranes of the two osmotic cells are to be selected so that the values for $\sigma_1$ and $\sigma_1'$ or $\sigma_2$ and $\sigma_2'$ are sufficiently different. The constant value K for a specified osmotic cell can be determined by calibration.

The short-term mixing of the solutions which occurs during the exchange of solutions in a container or in a pipeline can lead to a situation in which the initial pressure decrease in the osmotic cell is imprecisely defined. Only when the solutions have been completely switched will the linear portion of the pressure/time curve be reached, from which the initial slope for the execution of Method II can be determined.

If we overlook the variants of the Methods Ia and Ib, then alternative Method IIa makes possible a more rapid determination of the concentrations of the two substances than Methods Ia and Ib, since in the latter, the course of the total pressure curve must wait until the final value $P_E$ is reached. For this purpose, however, in the execution of Method IIa (as with the Method IIb), two osmotic cells are necessary. The execution of Method Ia or Ib, on the other hand, requires only a single osmotic cell each.

Even according to Method IIb, in which the parallel measurement is made via the determination of the pressure difference $(P_E - P_{min})$ or $(P_O - P_E)$, a more rapid determination of the concentration of a substance is possible if the concentration of one of the substances is constant and only the concentration of the other substance is to be measured.

In addition, according to Methods IIa and IIb, the time at which a solution containing two substances arrives can be determined, for example, at the measurement point of a pipeline into which water initially flows. For this purpose, the determination of the sum $X_1$ (or $X_2$) is sufficient for the determination of the time.

Of course, if the primary interest is not in the determination of the concentration of the substances, but in the determination of the time of a change of concentration of a solution in a container or in a pipe, Method II can be used without a parallel measurement, that is, the pressure decrease in the osmotic cell is determined by means of only one osmotic cell. In this manner, an osmotic cell can be used as a control or alarm apparatus The determination of the time according to Method II is also possible when the initial slope $(dP/dt)_{t=0}$ does not display a linear dependence on the concentrations, which is possible in the range of very high concentrations, and can lead to a hyperbolic shape for the calibration curves. A non-linear dependence may primarily indicate a concentration dependence of the hydraulic conductivity of the membrane ($L_P$) or effects of unstirred layers. A determination of concentration according to Method II is possible in this case, by diluting the solution to be tested so that there is again a linear relationship or by calculating, from ($P_O - P_E$), first $C_{imp}^o$, and then determining a calibration curve in the expected range of concentration of $C_s^o$ with solutions which already contain the impermeable substance in the correct concentration.

Applications for the determination of the concentration of substances are specifically the determination of low-molecular, permeable substances and high-molecular, impermeable substances. One application, for example, is the determination of the concentration of (permeable) alcohol and (impermeable) sugar during alcoholic fermentation. Such a determination is important both for the production of alcoholic beverages and also for the production of industrial alcohol. The methods described are also applicable to the determination of blood alcohol levels in human beings.

Other applications are the determination of the concentration of organic solvents in aqueous solutions, for example, of ethanol, methanol, propanol, esters, ether, acetone, etc., as required for certain chemical processes. Another area of application in the chemical industry is the determination of solvent residues, salts and other harmful substances in waste water.

The methods described can also be used for the monitoring of dialysis processes.

A special application for Method II, and possibly for the special variants of Methods Ia and Ib, lies in the rapid detection of a change in a solution, such as can occur in a brewery or in other sectors of the foods industry when there is a change between a cleaning agent, for example, water, and a product, for example, beer.

As a result of the rapid determination of the time of the solution change at a given point, product losses can be severely limited. Method II, moreover, can be applied in connection with only one osmotic cell as a warning system, for example, to detect leaks in tanks, pipelines, etc., on the basis of rapid changes in concentration.

For an apparatus for the execution of the methods described, a suitable measurement head, identified as measurement head "A" in FIG. 1, comprises an osmotic cell with a rigid wall, whose membrane delimits this cell at least partly on the outside, and which has a pressure measurement apparatus for the measurement of the hydrostatic pressure in the osmotic cell. Its membrane has the highest possible modulus of elasticity, the highest possible conductivity for the solvent, and a sufficiently high rejection capability for the substances in the solution to be tested.

The measurement head "A", for the execution of the method described, can be located on or in a container, or on or in a pipeline (or a bypass line), with the membrane turned towards the inside of the chamber into which, in an alternating fashion, the solution to be tested (or a diluted partial solution of the same) and the solution used to set the working pressure $P_O$ are introduced for the length of time required for the test.

Another measurement head, identified as measurement head "B", is suitable for the execution of the methods described in an apparatus for the determination of the concentration of substances dissolved in a solvent, which comprises an osmotic cell with a pressure measurement apparatus for the measurement of the hydrostatic pressure in the osmotic cell and a container, which is in communication with the osmotic cell, so that its inside is adjoined by the membrane of the osmotic cell. The osmotic cell has a rigid wall made of metal or plastic. The container is equipped with a feed and discharge line for the solution for the establishment of the working pressure $P_O$, for the solution to be tested and for the calibration solutions, if any, whereby the feed and discharge line as well as the inside of the container are designed so that the solutions fed into them can be introduced into the container as rapidly as possible. The membrane also exhibits the highest possible modulus of elasticity, the highest possible conductivity for the solvent and a sufficiently high retention capacity for the substances in the solution to be tested. A hyperfiltration membrane is appropriate. The membrane of the measurement heads "A" or "B" can be a hollow fiber membrane. The inside of the fibers can thereby serve as an osmotic cell or, in the case of measurement head "B", as the container. Of course, bundles of hollow fibers can also be used.

With measurement head "B" (the measurement head with integrated container), the solutions to be brought into communication by means of the membrane with the osmometer solution, that is, the solution required to establish the working pressure $P_O$ and the solution to be tested, as well as any calibration solution, are introduced into the container. The feed line and the inside of the container are designed so that the exchange of the solutions takes place both completely and as rapidly as possible. Unstirred layers can be minimized by rapid, continual flushing with the solutions.

The osmotic cell appropriately exhibits a feed and discharge line for the osmometer solution. The inside of the osmotic cell should be kept as small as possible, since experience has shown that such a small size is most suitable for the achievement of high $\epsilon$-values for the cell. On the other hand, agitation (convection) of the osmometer solution during the measurement is desirable, to minimize effects caused by unstirred layers on the membrane surface. For this purpose, an osmotic cell can also be equipped with a stirrer. The stirrer should take up as little space as possible, however. Such a stirrer preferably comprises a magnetic stirrer of the type comprising a small magnet or metallic object disposed within the osmotic cell and manipulated by a rotating magnetic field generated external to the osmotic cell. An alternative, in which no stirrer is necessary, consists of designing the osmotic cell so that its dimensions are on the order of magnitude of the expected thicknesses of the unstirred layers.

Specifically for the execution of Methods Ia and Ib, it is also appropriate if the ratio of the volume of the osmotic cell to the effective surface of the membrane is as small as possible, thereby guaranteeing the most rapid possible exchange of the solvent and the permeable substances in the solution to be tested by the membrane. This ratio should be no greater than 0.2 mm. If the membrane is not sufficiently rigid, it has been shown to be appropriate to reinforce the membrane with metal grids.

With regard to a general control of the measurement heads "A" or "B", not only for rigidity of the osmotic cells, but also for the determination of the modulus of elasticity ε of the osmotic cell for the method, in which the determinations are made according to Equations 3 and 4, it is appropriate to provide an apparatus for the controlled volume change of the osmotic cell. With such an apparatus, for example, the volume of the osmotic cell can be very precisely varied within certain limits by inserting and extracting a control rod, and the change in volume can be measured by means of a micrometer. With a closed osmotic cell, this causes pressure changes which are detected by means of the pressure apparatus. With a known volume of the osmotic cell, the elasticity of the osmotic cell (the volumetric elastic modulus ε, whereby $\varepsilon = V(\Delta P/\Delta V)$ can be determined. An alternative procedure to determine ε is to use Equation 4. If $C_{im}^i$ and $C_{imp}^o$ are known, ε can be evaluated, if $P_O$-$P_E$ is measured.

In another variant of the measurement head "A" or "B", the pressure measurement apparatus emits electrical output signals, which are a measure of the concentration of the substances in the solution to be tested.

For the use of measurement head "A", which comprises an osmotic cell without an additional container for the solution to be tested, a suitable apparatus includes a container on which the measurement head is installed, delimiting the inside of the container with its membrane, and which can be filled as required with a solution for the establishment of the working pressure $P_O$, with the solution to be tested and, if necessary, with calibration solutions. Of course, the container can also be a pipeline.

A suitable apparatus for measurement head "B" is one in which there is a storage container in communication with the feed line for the container with the measurement head for the solution used to establish the working pressure $P_O$, and possibly for the calibration solution, and a storage container for the osmometer solution in communication with the feed line for the osmotic cell, and on which, moreover, there is a recipient or a pipeline for one containing the solution to be tested in communication with the feed line for the container of the measurement head "B".

If a measurement head "A" or "B" is used for the apparatus, whose pressure measurement device emits electrical signals, then the curve of the measurement values can be printed out.

The devices can be selected independently of the type of measurement head used and the type of method applied, and, therefore, independently of whether one or two measurement heads are used, and as a measurement apparatus which can be moved or installed at a fixed point, for example, as part of an installation for the execution of a given process, such as alcoholic fermentation. It may be appropriate to have a control apparatus for control of automatic operation of the device, whereby alternately at pre-determined intervals of time, the solution intended to establish the working pressure $P_O$ and the solution to be tested are charged into the container of the measurement head "B" or into the container, to which measurement head "A" is attached. If there are two measurement heads for the execution of Method II, then, of course, one measurement head "A" and one measurement head "B" can also be used.

Another very advantageous apparatus is one in which there is another control and/or monitoring apparatus which receives the electrical output signals of the measurement head "A" or "B" or, when Method II is used, of the measurement heads "A"—"A", "A"-"B", or "B"—"B", and uses them to control and or monitor processes which have an operational relationship to the concentration of the substances to be tested. In addition to a monitoring of the processes, certain desired values of the concentration of the substances can be electronically regulated during such processes. Such processes include, for example, alcoholic fermentation, in which the concentration of alcohol (permeable) and the concentration of sugar (impermeable) can give some indication of the status of the fermentation or the monitoring of solvent concentrations in waste water. When the methods described are used, traditional analytical concentration determinations are no longer necessary. In the case of the application of Methods Ia and Ib, the cycle time in which the measurement can be repeated is a function of, on one hand, the test time which can be several minutes, and on the other hand, the processes themselves which are to be monitored. The test time is a function of the physical properties of the membrane (conductivity for the solvent and the dissolved substances), and of the measurement head "A" or "B" (volume/surface ratio of the osmotic cell; volumetric elastic modulus), and can therefore be adjusted to serve the measurement situation at hand.

The present invention will now be described, reference being had to FIGS. 5–13.

Figure 5:
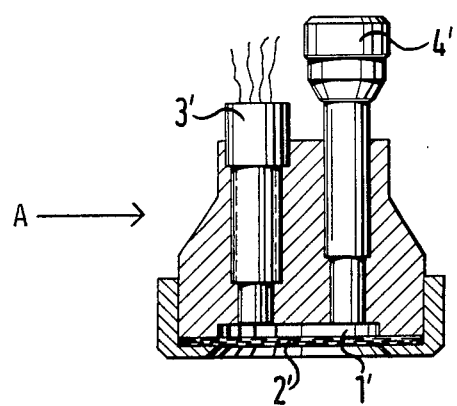

The measurement head "A", illustrated in FIG. 5, consists of an osmotic cell 1' with a membrane 2' and a pressure measurement apparatus 3' with a pressure sensor which transmits electrical signals. There is also an apparatus 4' for the controlled modification of the volume of the osmotic cell 1', consisting of a micrometer screw with a precision control rod, by means of which a measurable change in the volume of the osmotic cell can be made. This controlled volume change, which results in a change in the pressure in the osmotic cell, can be used to check the rigidity of the osmotic cell by means of the pressure measurement transformer, or to determine the modulus of elasticity of the cell.

Figure 6:
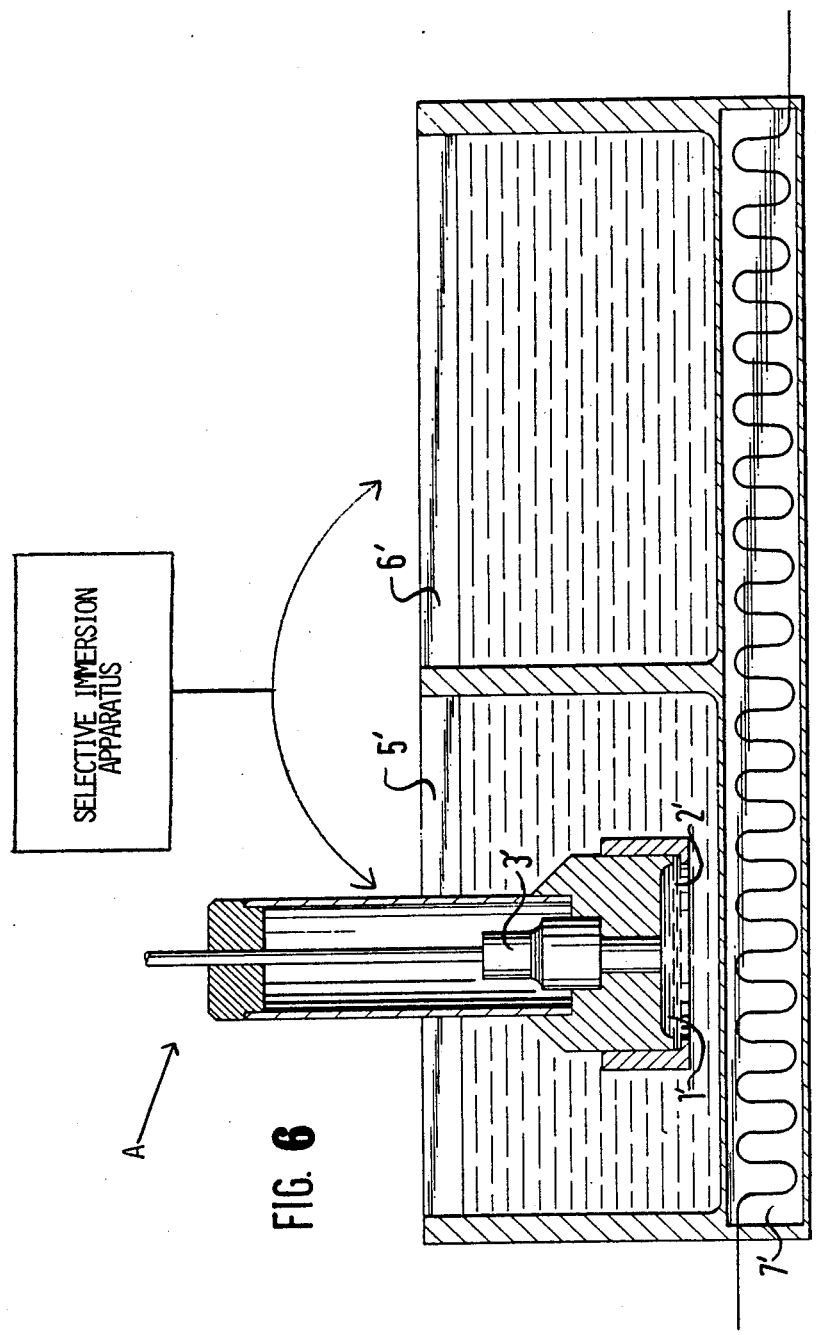

FIG. 6 shows an apparatus with a measurement head "A" of the type illustrated in FIG. 5, consisting of an osmotic cell 1' and pressure measurement apparatus 3' in use. There is no apparatus for controlled volume change in this embodiment.

There can be optional vessels 5' and 6' for the reference solution and for the solution to be tested, respectively. The solutions in the two vessels are kept at a constant temperature by means of a thermostatically controlled heating element 7'.

To determine the concentration of dissolved substance in the solution in the vessel 6', the measurement head is first immersed in the reference solution in vessel 5' to establish the working pressure $P_O$. After the working pressure $P_O$ has been established and determined, the measurement head is immersed in the solution to be tested in vessel 6', whereupon the minimum pressure $P_{min}$ is initially established, and then the final pressure $P_E$.

For calibration, a standard solution is used in the vessel 6' instead of the solution to be tested.

Figure 7:
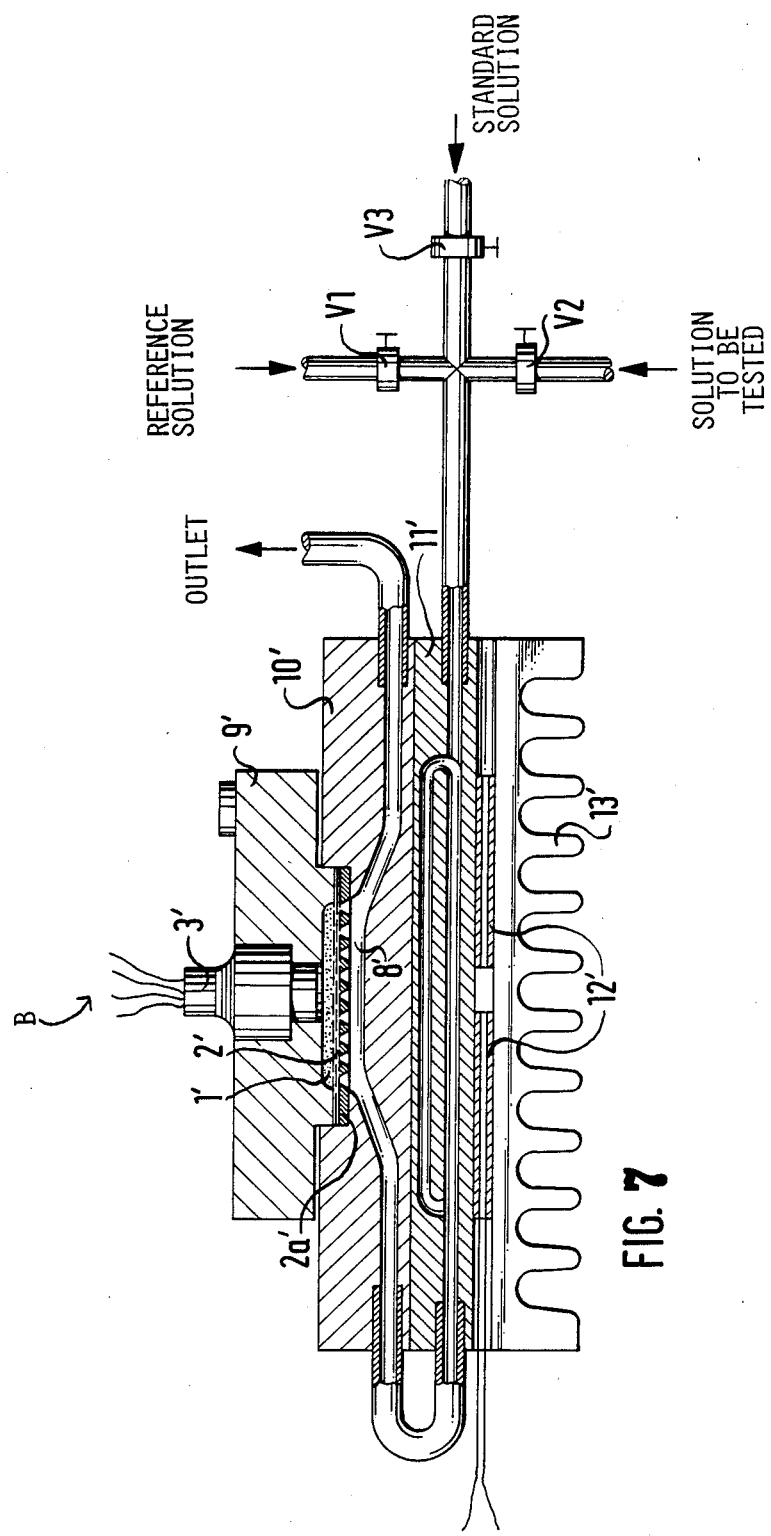

FIG. 7 shows a measurement head "B" with an osmotic cell 1', membrane 2' with support grid 2a', and pressure measurement apparatus 3', integrated into which is a vessel 8' to hold the solutions along with its housing, consisting of the elements 9' and 10' made of steel. Attached to the element 10' is an apparatus to keep the temperature constant, consisting of the copper heat exchanger plate 11', in which the feed line to the vessel 8' runs in a spiral, of a Peltier cell consisting of two Peltier elements 12' and their attached temperature line 13'.

To establish the working pressure, first of all a suitable reference solution is introduced through the vessel 8' with an open valve V1 (valves V2 and V3 are closed), whereby this solution comes into communication across the membrane 2' with the osmometer solution in the osmotic cell. After the establishment and determination of the working pressure $P_O$, with valve V2 then opened (valves V1 and V3 are closed), the solution to be tested is introduced into vessel 8', whereupon a minimum pressure $P_{min}$ and a final pressure $P_E$ are established. For calibrations, a standard solution is introduced via the vessel 8', and via valve V3, while valves V1 and V2 are closed.

Figure 8:
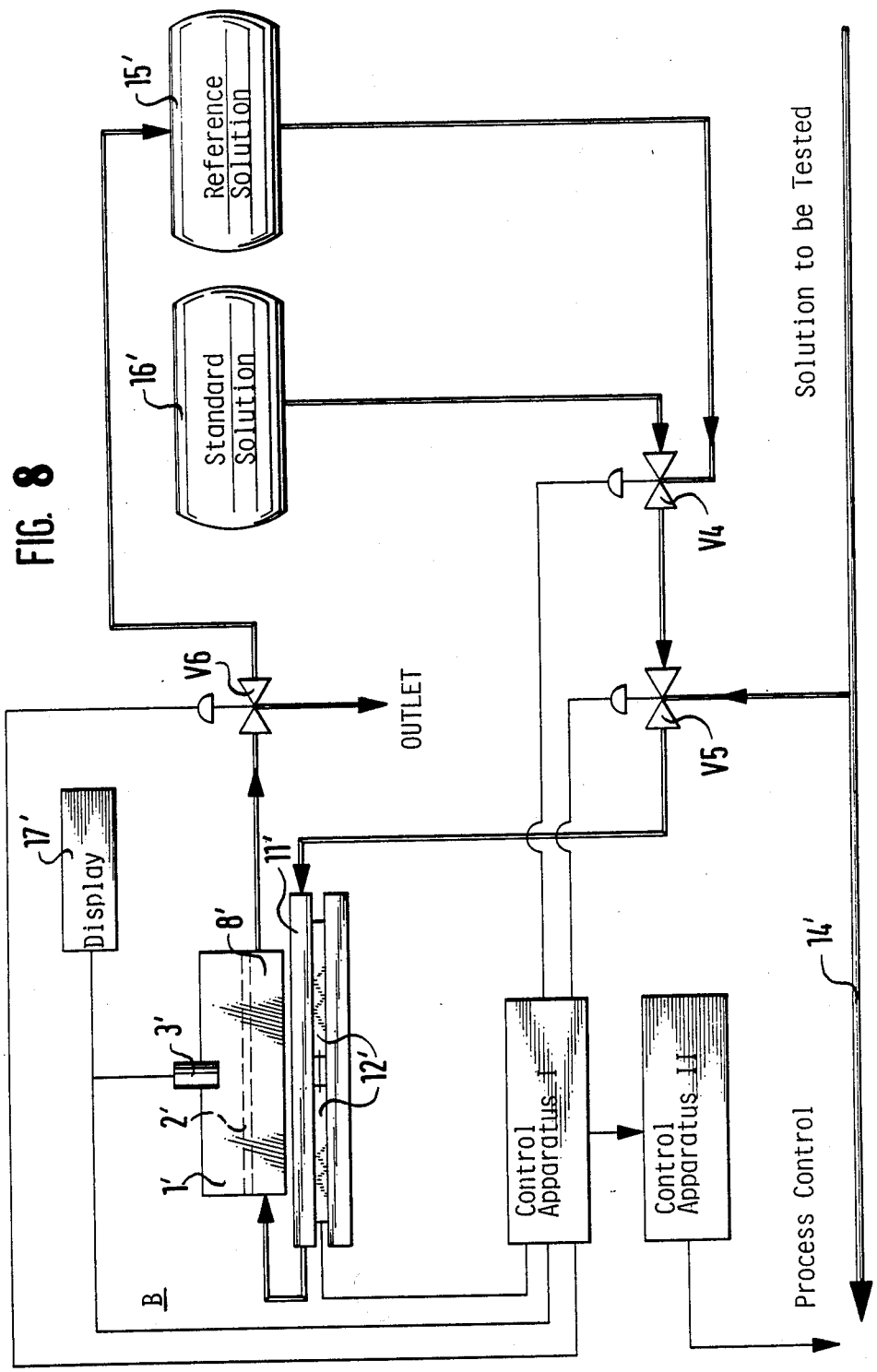

FIG. 8 shows an apparatus with a measurement head "B" of the type illustrated in FIG. 7, which is used for the determination of the concentration of substances in a solution flowing 14'. The valves V4 and V5' which have the same function as the valves V1 and V2 illustrated in FIG. 7, are designed as remote-control check valves, which are connected electrically to the control apparatus I. By means of this control apparatus I, at predetermined intervals, for the establishment of a working pressure $P_O$, reference solution is transported out of the storage vessel 15' through the valves V4 and V5 through the vessel 8' (valve V6 closed). Thereafter, the solution to be tested is fed out of the line 14' via the valve V5 (with valve V4 closed) into the vessel 8'. Of course, at longer intervals, standard solutions from the storage vessel 16', via the valves V4 and V5, can also be admitted to the vessel 8' by means of the control apparatus I.

As also shown in FIG. 8, the electrical output signals from the pressure measurement apparatus are displayed on an indicator 17' and transmitted to the control apparatus I. The process is controlled by a control apparatus II, which is electrically connected to the control apparatus I, as a function of the measurements taken.

Figure 9:
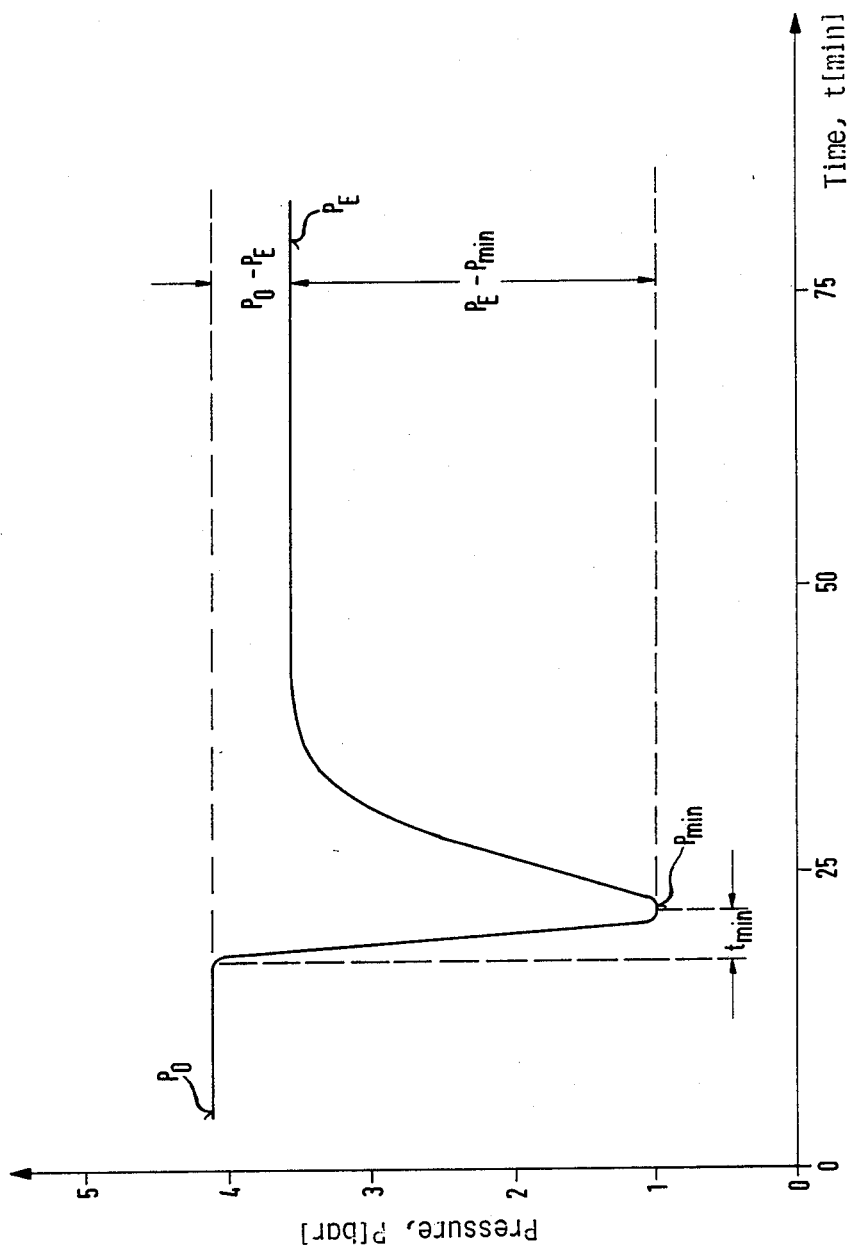

FIG. 9 shows the typical pressure curve in the osmotic cell after the change from the reference solution to the solution to be tested or the standard solution.

Embodiments:

The solutions indicated below were tested using a measurement head of the type illustrated in FIG. 7. The measurement head consisted of a stainless steel housing. The ratio of the volume of the osmotic cell to the effective surface of the membrane was 0.1 mm. The membrane was an asymmetrical polyamide membrane (reverse osmosis membrane) with a separation limit of 50 Daltons. This osmometer membrane is completely impermeable for potassium hexacyanoferrate (II) ($K_4[Fe(CN)_6]$). The solutions were kept at 25° C. for the measurement.

1. Process Ia was used, according to which the concentrations of the substances tested are given on the basis of calibrated values.

Determination of a Low Concentration of a Permeable Substance (Ethanol) and a High Concentration of a Practically Impermeable Substance (NaCl).

Embodiment 1a

The five calibrated values indicated below were determined to plot a calibration curve (FIG. 6). A reference solution without any alcohol component (only 300 mOsmol NaCl) was used for the first calibrated value.

The osmometer solution contained 300 mOsmol NaCl+63 mOsmol potassium hexacyanoferrate (II) ($K_4[Fe(CN)_6]$). The working pressure was $P_O=0.96$ bar.

The ethanol concentration of the standard solutions, which all contain 300 mOsmol, was selected so that their difference from the ethanol concentration of the reference solutions corresponded to the $\Delta C_S^O$ values indicated below.

The change the reference solutions to the corresponding standard solutions yielded the following results:

| Change in the alcohol concentration, $\Delta C_S^O$ | | Maximum change in the osmometer pressure ($P_O-P_{min}$) |
|---|---|---|
| (mM) | (% o)(tenths of %) | (bar) |
| 22 | 1.01 | 0.192 |
| 46 | 2.11; 2.11 | 0.436; 0.404 |
| 66 | 3.03 | 0.620 |
| −46 | −2.11 | −0.440 |

The negative value of $\Delta C_S^O$ and ($P_O - P_{min}$) results from the fact that the osmometer was first balanced against a calibration ethanol solution of 46 mM ethanol, which was then replaced by the reference solution as the standard solution (300 mOsmol NaCl).

Figure 10:
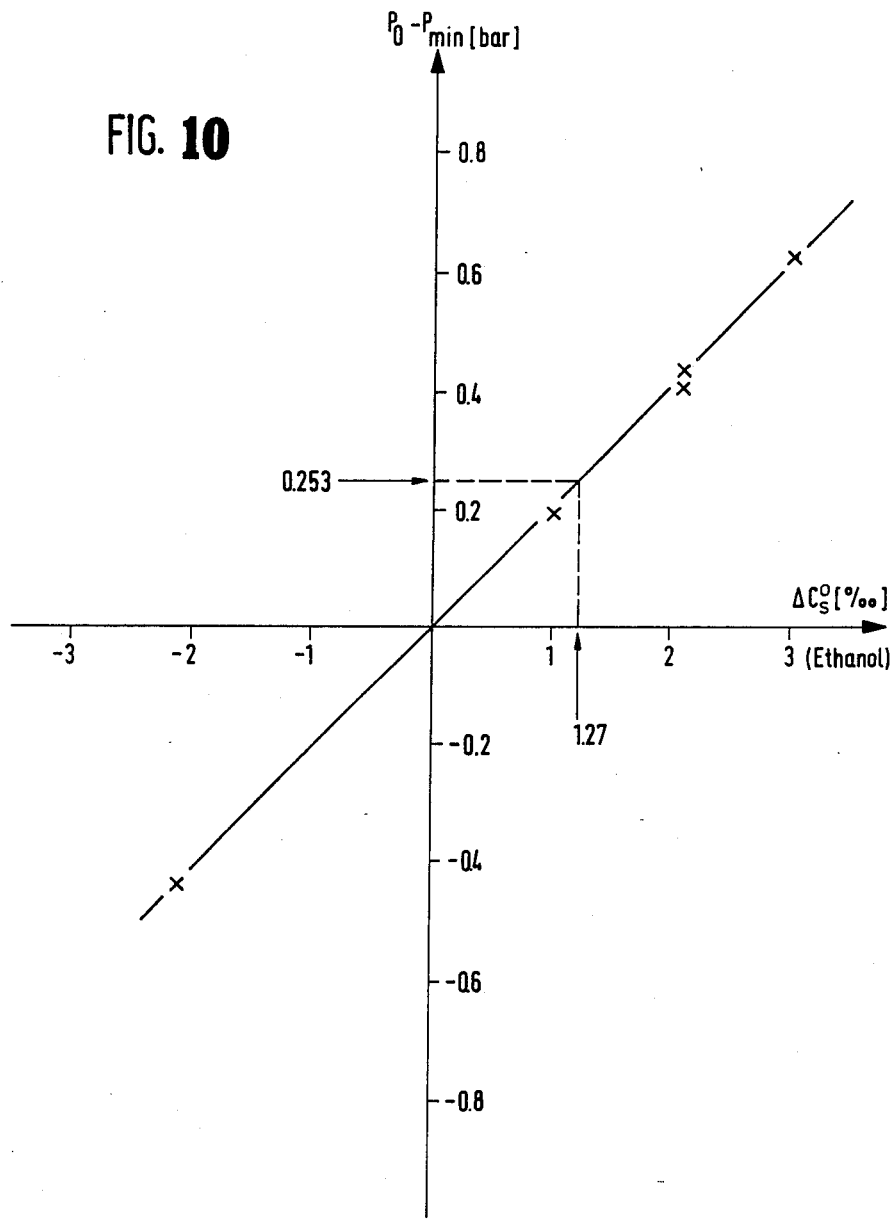
Figure 11:
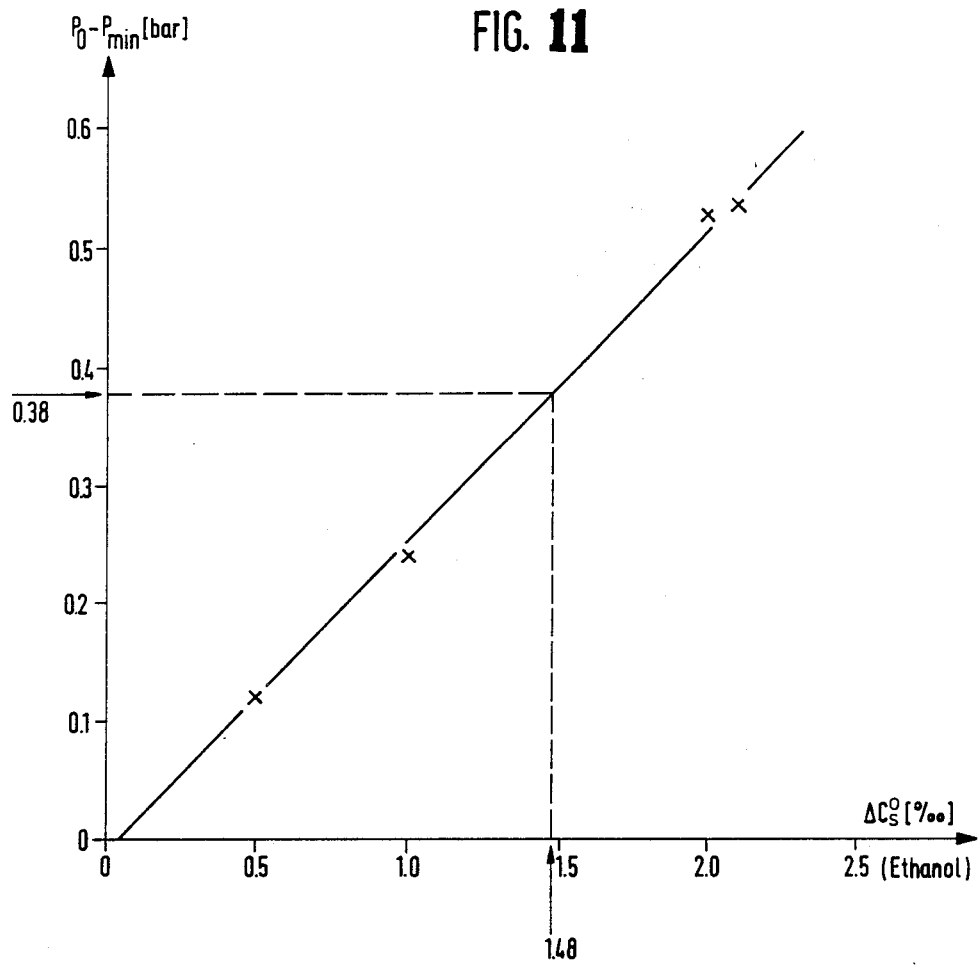
Figure 12:
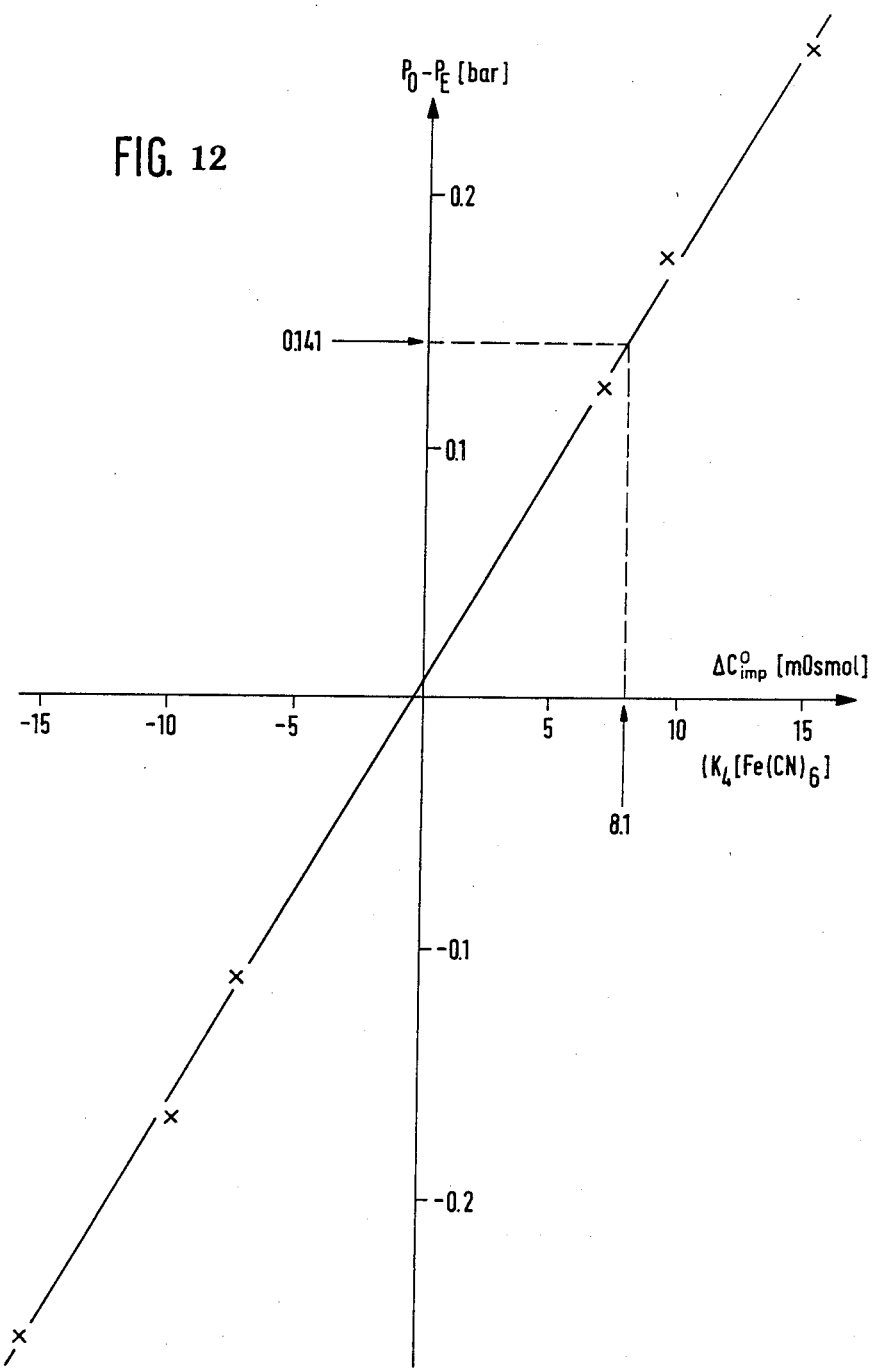

The measurement data yielded the calibration curve shown in FIG. 10.

Using the same osmometer solution, and on the basis of the calibration curved determined, the ethanol concentration of a solution also containing 300 mOsmol was determined, whose originally weighed-in ethanol concentration was 1.26 %o (tenths of %). The measured maximum pressure change of 0.253 bar resulted in a measured ethanol concentration of 1.27 %o (tenths of %).

Embodiment 1b:

To plot a calibration curve (FIG. 7), four calibrated values were determined.

| Osmometer solution: | 300 mOsmol NaCl + 61 mOsmol $K_4([Fe(CN)_6])$ |
|---|---|
| Working pressure: | $P_O = 0.66$ bar |
| Reference solution: | Blood plasma with an osmosis pressure of 320.9 mOsmol. |

The calibration with blood plasma with various alcohol concentrations yielded:

| Alcohol concentration in blood plasma (% o) | Maximum pressure change (bar) |
|---|---|
| 0.5 | 0.118 |
| 1.0 | 0.240 |
| 2.0 | 0.528 |
| 2.1 | 0.536 |

From the calibration curve (FIG. 7), we get, for a plasma with an originally weighed-in quantity of 1.45 %o ethanol, for a maximum pressure change of 0.380 bar, a measured alcohol concentration of 1.48 %o.

2. Determination of Small Concentration Changes (Fluctuations) of an Impermeable Substance and High Concentrations of a Practically Impermeable Substance (NaCl)

Embodiment 2:

| Reference solution: | 300 mOsmol NaCl |
|---|---|
| Osmometer solution: | 300 mOsmol NaCl + |

-continued

| | |
|---|---|
| Working pressure: | 60 mOsmol (K$_4$[Fe(CN)$_6$])<br>0.95 bar |

The change of the reference solution for the calibrated solutions (300 mOsmol NaCl+(K$_4$[Fe(CN)$_6$]) with different concentrations of the impermeable substance (K$_4$[Fe(CN)$_6$]) yielded the calibrated values:

| Change in concentration of (K$_4$[Fe(CN)$_6$]) in the standard solution (mOsmol) | Stationary pressure change in the osmometer, (P$_O$-P$_E$) (bar) |
|---|---|
| 7 | 0.124 |
| 9.4 | 0.176 |
| 15.2 | 0.258 |
| −7 | −0.112 |
| −9.4 | −0.168 |
| −15.2 | −0.257 |

Negative values indicate changes during a switch from standard solutions to the reference solution (300 mOsmol NaCl). The calibration curve from these date (FIG. 8) gives, for a stationary pressure change of 0.141 bar, a solution which in addition to 300 mOsmol NaCl, contained an originally weighed-in quantity of 8.0 mOsmol NaCl, for a measured concentration of 8.1

3. Precision Measurement of the Concentration of Permeable Substances in a Solution Embodiment 3:

The determination is made by comparison with a reference solution with a precisely known concentration, which varies little from that of the solution to be measured.

| | |
|---|---|
| Reference solution: | 38 wt % ethanol in water |
| Osmometer solution: | 38 wt % ethanol + 63 mOsmol (K$_4$[Fe(CN)$_6$]) |

The addition of ethanol to the reference solution gives standard solutions which result in the following maximum pressure changes in the osmometer:

| Alcohol concentrations of the standard solutions (wt %) | Maximum pressure changes in the osmometer (bar) |
|---|---|
| 38.197 | 0.056 |
| 38.588 | 0.132 |
| 38.977 | 0.207 |

The calibration curve (FIG. 9) gives for an aqueous ethanol solution (weighed-in amount 38.655%) with a $P_O - P_{min} = 0.142$ bar, a measured concentration of 38.654% ethanol.

In summary, the present invention features an improved process for testing a test solution which includes a solvent and at least one of a first (relatively permeable) substance dissolved in the solvent and a second (relatively impermeable) substance dissolved in the solvent. The present invention has particular application to the testing of solutions having relatively high concentrations of the first and/or second substances.

In general, the present invention includes the steps of providing a first osmotic membrane which has differing and distinct permeabilities with respect to the solvent, the first substance and the second substance, the osmotic membrane being significantly more permeable with respect to the solvent than with respect to the first substance, and being significantly more permeable with respect to the first substance than with respect to the second substance. One side of the osmotic membrane is exposed to an osmometer solution having concentrations of the first and second substances which differ from the approximate expected concentrations of the first and second substances in the test solution, respectively, by not more than a predetermined difference. The second side of the osmotic membrane is then exposed to a reference solution having a concentration of the second substance which differs from the concentration of the second substance in the osmometer solution by no more than a second predetermined difference. A working pressure, $P_O$, is then determined for the osmometer solution while the other side of the osmotic membrane is exposed to the reference solution. The reference solution is then replaced with the test solution, and thereafter, at least one pressure change characteristic of the osmomer solution is determined. Using the at least one determined pressure change characteristic of the osmometer solution, at least one of the concentrations of the first and second substances in the test solution is then determined.

By maintaining the concentration differences of the first and second substances of the osmometer solution and the test solution within the range defined by the first predetermined difference, and by maintaining the difference in the concentration of the second substance between the reference solution and the osmometer within the range defined by the second predetermined difference, it has been discovered that a substantially linear and/or predictable relationship is established between the pressure change characteristics of the osmometer solution and the concentrations of the first and second substances in the test solution, even in the situation where the concentrations of the first and second substances in the test solution are expected to be relatively high. Therefore, an improved degree of precision is afforded by the present invention, particularly as regards the measurement of relatively high concentrations of substances in the test solution.

Preferably, the first and second predetermined differences are maintained at 70 mOsm and 80 mOsm, respectively.

As discussed above, the prior art describes a number of process variants (e.g., methods Ia, Ib, IIa and IIb) which have application to the measurement of the concentrations of substances dissolved in a solvent. The present invention is seen to have application to at least those prior art processes described above, particularly in the situation wherein the test solution may be expected to have relatively high concentrations of substances dissolved therein.

The invention as described hereinabove in the context of the preferred embodiments is not to be taken as limited to all of the provided details thereof, since modifications and variations thereof may be made without departing from the spirit and scope of the invention.

What is claimed is:

1. A process for testing a test solution, said test solution comprising a solvent, and at least one of a first substance dissolved in said solvent and a second substance dissolved in said solvent, said test solution having an approximate expected concentration of said first substance and an approximate expected concentration of said second substance, said process comprising the steps of:
(a) providing a first osmotic membrane, said first osmotic membrane having differing and distinct permeabilities with respect to said solvent, said first substance and said second substance, said first osmotic membrane being significantly more permeable with respect to said solvent than with respect to said first substance, and said first osmotic membrane being significantly more permeable with respect to said first substance than with respect to said second substance;
(b) exposing a first side of said first osmotic membrane to an osmometer solution, said osmometer solution having concentrations of said first and second substances which differ from said approximate expected concentrations of said first and second substances of said test solution, respectively, by not more than a first predetermined difference;
(c) exposing the second side of said first osmotic membrane to a reference solution, said reference solution having a concentration of said second substance which differs from said concentration of said second substance of said osmometer solution by not more than a second predetermined difference;
(d) determining a working pressure, $P_O$, existing on said first side of said first osmotic membrane exposed to said selected osmometer solution while said second side of said first osmotic membrane is exposed to said reference solution;
(e) replacing said reference solution with said test solution
(f) thereafter, determining at least one pressure change characteristic of said osmometer solution; and
(g) using said at least one determined pressure change characteristic of said osmometer solution to determine at least one of said concentrations of said first and second substances in said test solution.

2. The process for testing a test solution according to claim 1, wherein said step (g) of using said at least one pressure change characteristic of said osmometer solution to determine at least one of said concentrations of said first and second substances in said test solution comprises the steps of:
(g1) determining the final pressure, $P_E$, existing on said first side of said first osmotic membrane exposed to said osmometer solution following replacement of said reference solution with said test solution;
(g2) determining a difference, $P_O - P_E$; and
(g3) using said difference, $P_O - P_E$, to determine said concentration of said second substance of said test solution.

3. The process for testing a test solution according to claim 1, wherein said step (g) of using said at least one pressure change characteristic of said osmometer solution to determine at least one of said concentrations of said first and second substances in said test solution comprises the steps of:
(g1) determining the minimum pressure, $P_{min}$, existing on said first side of said first osmotic membrane exposed to said osmotic solution following replacement of said reference solution with said test solution;
(g2) determining the final pressure, $P_E$, existing on said first side of said first osmotic membrane exposed to said osmotic solution following replacement of said reference solution with said test solution;
(g3) determining a difference, $P_E - P_{min}$; and
(g4) using said difference, $P_E - P_{min}$, to determine said concentration of said first substance of said test solution.

4. The process for testing a test solution according to claim 1, wherein said step (g) of using said at least one pressure change characteristic of said osmometer solution to determine at least one of said concentrations of said first and second substances in said test solution comprises the steps of:
(g1) determining the minimum pressure, $P_{min}$, existing on said first side of said first osmotic membrane exposed to said osmotic solution following replacement of said reference solution with said test solution;
(g2) determining the final pressure, $P_E$, existing on said first side of said first osmotic membrane exposed to said osmotic solution following replacement of said reference solution with said test solution;
(g3) determining difference, $P_O - P_{min}$;
(g4) determining another difference, $P_E - P_{min}$;
(g5) using said difference, $P_O - P_{min}$, to determine said concentration of said second substance of said test solution; and
(g6) using said other difference, $P_E - P_{min}$, to determine said concentration of said first substance of said test solution.

5. The process for testing a test solution according to claim 1, comprising the additional step of calibrating sad testing process by exposing said second side of said first osmotic membrane to a plurality of calibration solutions, said plurality of calibration solutions having a known concentration of at least one of said first and second substances.

6. The process for testing a test solution according to claim 2, comprising the additional step of calibrating said testing process by exposing said second side of said first osmotic membrane to a plurality of calibration solutions, said plurality of calibration solutions having a known concentration of at least one of said first and second substances.

7. The process for testing a test solution according to claim 3, comprising the additional step of calibrating said testing process by exposing said second side of said first osmotic membrane to a plurality of calibration solutions, said plurality of calibration solutions having a known concentration of at least one of said first and second substances.

8. The process for testing a test solution according to claim 4, comprising the additional step of calibrating said testing process by exposing said second side of said first osmotic membrane to a plurality of calibration solutions, said plurality of calibration solutions having a known concentration of at least one of said first and second substances.

9. The process for testing a test solution according to claim 1, wherein said first predetermined difference in said step (b) is approximately equal to 70 mOsm, and wherein said second predetermined difference in said step (c) is approximately equal to 80 mOsm.

10. The process for testing a test solution according to claim 2, wherein said first predetermined difference in said step (b) is approximately equal to 70 mOsm, and wherein said second predetermined difference in said step (c) is approximately equal to 80 mOsm.

11. The process for testing a test solution according to claim 3, wherein said first predetermined difference in said step (b) is approximately equal to 70 mOsm, and wherein said second predetermined difference in said step (c) is approximately equal to 80 mOsm.

12. The process for testing a test solution according to claim 4, wherein said first predetermined difference in said step (b) is approximately equal to 70 mOsm, and wherein said second predetermined difference in said step (c) is approximately equal to 80 mOsm.

13. The process for testing a test solution according to claim 9, wherein said concentration of said second substance in said osmometer solution exceeds said concentration of said second substance in said reference by not more than said predetermined difference of 80 mOsm.

14. The process for testing a test solution according to claim 9, wherein said first predetermined difference in said step (b) is 20 mOsm, and wherein said process comprises the additional step of maintaining said osmometer solution, said reference solution and said test solution at a substantially constant temperature at least when said osmometer, reference and test solutions are in contact with said first osmotic membrane.

15. The process for testing a test solution according to claim 1, wherein said step (g) ff using said at least one pressure change characteristic of said osmometer solution to determine at least one of said concentrations of said first and second substances in said test solution comprises the steps of:
(g1) determining the minimum pressure, $P_{min}$, existing on said first side of said first osmotic membrane exposed to said osmotic solution following replacement of said reference solution with said test solution;
(g2) determining a time period, $t_{min}$, at which said minimum pressure occurs following replacement of said reference solution with said test solution;
(g3) determining a rate constant $k_s$ for any exponential pressure increase which occurs following establishment of said minimum pressure, $P_{min}$;
(g4) determining a final pressure, $P_E$;
(g5) determining said concentration of said second substance in said test solution, $C_s^o$, according to the equation:

$$P_E - P_{min} = \sigma_s RT C_s^o \cdot \exp(-k_s t_{min})$$

where $R = 8.31434$ J/K°mol,

T = absolute temperature and $\sigma_s$ = reflection coefficient of s; and
(g6) determining said concentration of said first substance in said test solution, $C_{imp}^o$, according to the equation:

$$P_O - P_E = RT \cdot C_{imp}^o.$$

16. The process for testing a test solution according to claim 15, wherein said osmotic solution is contained in an osmotic cell having a volumetric elasticity modulus of $\epsilon$, wherein said concentration of said first substance in said test solution, $C_s^o$, is determined according to the equation:

$$P_E - P_{min} = \frac{\epsilon}{\epsilon + RT \cdot C_{imp}^i} \cdot \sigma_s \cdot RT \cdot C_s^o \cdot \exp(-k_s \cdot t_{min})$$

and wherein said concentration of said second substance in said test solution $C_{imp}^o$ is determined according to the equation:

$$P_O - P_E = \frac{\epsilon}{\epsilon + RT \cdot C_{imp}^i} RT \cdot C_{imp}^o.$$

17. The process for testing a test solution according to claim 16, comprising the additional steps of determining a rate constant, $k_w$, and determining a temporal change, $(d^2P/dt^2)_{min}$, of the slope of the pressure/time curves in the region of said minimum pressure, $P_{min}$, and wherein said final pressure $P_E$ is determined according to the equation:

$$k_s \cdot k_w = \frac{1}{P_E - P_{min}} (d^2P/dt^2)_{min}.$$

18. The process for testing a test solution according to claim 1, wherein said step (g) of using said at least one pressure change characteristic of said osmometer solution to determine at least one of said concentrations of said first and second substances in said test solution comprises the steps of:
(g1) determining an initial rate of change, $(dP/dt)_{t=0}$, of the pressure existing in said osmometer solution on said first side of said first osmotic membrane;
(g2) using the equation:

$$(dP/dt)_{t=0} = -\frac{A_o}{V_o} \cdot Lp \cdot \epsilon \cdot RT(\sigma_1 \cdot C_1 + \sigma_2 \cdot C_2)$$

to determine a result:

$$X_1 = \sigma_1 \cdot C_1 + \sigma_2 \cdot C_2$$

where:
$A_o$ is the effective surface area of the membrane
$V_o$ is the volume of the osmotic cell;
Lp is the hydraulic conductivity of the membrane;
$\epsilon$ is the volumetric elastic modulus of the osmotic cell;
R = 8.31434 J/°K. mol;
T is the absolute temperature;
$\sigma_1$ is the reflection coefficient of the substance No. 1;
$C_1$ is the concentration of the substance No. 1;
$\sigma_2$ is the concentration of substance No. 2; and
$C_2$ is the concentration of substance No. 2
and wherein said process additionally comprises the further steps of:
(h) performing said steps (a) through (g) using a second osmotic membrane having permeabilities with respect to said first and second substances which substantially differ from the permeabilities of said first osmotic membrane with respect to said first and second substances, respectively, to determine another result:

$$X_2 = \sigma_1' \cdot C_1 + \sigma' \cdot C$$

and (i) using said two determined results, $X_1$ and $X_2$, to determine said concentration of at least one of said first and second substances in said test solution.

19. The process for testing a test solution according to claim 18, wherein said step (h) to determine said other result $X_2$ is carried out according to said steps (g1) and (g2).

20. An apparatus for testing a test solution, said test solution comprising a solvent, and at least one of a first substance dissolved in said solvent and a second substance dissolved in said solvent, said apparatus comprising:

an osmotic cell comprising a cavity for containing an osmometer solution and an osmotic membrane defining a surface of said osmotic cell;

the ratio of the volume of said osmotic cell to the effective surface area of said osmotic membrane being a maximum of about 0.2 mm;

said osmotic membrane having a substantially high modulus of elasticity, a substantially high permeability with respect to said solvent and a substantially lower permeability with respect to said first and second substances;

at least one vessel;

means for selectively placing a reference solution and said test solution in said vessel;

means for interfacing said osmotic membrane with said reference and test solutions contained in said vessel; and means for maintaining, at a substantially constant temperature, the region of said interface of said osmotic membrane with said reference and test solutions.

21. The apparatus for testing a test solution according to claim 20, wherein said at least one vessel comprises a first vessel for containing said referenc solution and a second vessel containing said test solution, and wherein said means for interfacing comprises means for immersing said osmotic membrane, selectively, in said first and second vessels.

22. The apparatus for testing a test solution according to claim 20, wherein said means for selectively placing a reference solution and said test solution in said vessel and said means for interfacing comprise at least one feed line means for feeding a solution into said vessel, at least one discharge line means for discharging a solution from said vessel, means for selectively rapidly supplying said reference solution to said vessel through said feed line means, and means for selectively rapidly supplying said test solution to said vessel through said feed line means.

* * * * *